US011773391B2

(12) United States Patent
Chan et al.

(10) Patent No.: US 11,773,391 B2
(45) Date of Patent: Oct. 3, 2023

(54) THERAPEUTIC AND DIAGNOSTIC TARGET FOR SARS-COV-2 AND COVID-19

(71) Applicant: University of Pittsburgh—Of the Commonwealth System of Higher Education, Pittsburgh, PA (US)

(72) Inventors: Stephen Yu-Wah Chan, Pittsburgh, PA (US); LLoyd David Harvey, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 84 days.

(21) Appl. No.: 17/218,604

(22) Filed: Mar. 31, 2021

(65) Prior Publication Data
US 2021/0309998 A1    Oct. 7, 2021

Related U.S. Application Data

(60) Provisional application No. 63/003,571, filed on Apr. 1, 2020.

(51) Int. Cl.
C12N 15/113    (2010.01)
A61K 31/5377    (2006.01)
C07H 21/04    (2006.01)

(52) U.S. Cl.
CPC ........ *C12N 15/113* (2013.01); *A61K 31/5377* (2013.01); *C12N 15/1135* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,837,511 A | 11/1998 | Falck-Pedersen et al. | |
| 5,851,806 A | 12/1998 | Kovesdi et al. | |
| 5,994,106 A | 11/1999 | Kovesdi et al. | |
| 6,127,175 A | 10/2000 | Vigne et al. | |
| 6,482,616 B1 | 11/2002 | Kovesdi et al. | |
| 7,195,896 B2 | 3/2007 | Kovesdi et al. | |
| 8,058,069 B2 | 11/2011 | Yaworski et al. | |
| 8,101,348 B2 | 1/2012 | Tuschl et al. | |
| 8,450,298 B2 | 5/2013 | Mahon et al. | |
| 8,969,353 B2 | 3/2015 | Mahon et al. | |
| 9,227,917 B2 | 1/2016 | Anderson et al. | |
| 9,364,435 B2 | 6/2016 | Yaworski et al. | |
| 9,404,127 B2 | 8/2016 | Yaworski et al. | |
| 9,439,968 B2 | 9/2016 | Anderson et al. | |
| 9,556,110 B2 | 1/2017 | Mahon et al. | |
| 9,872,911 B2 | 1/2018 | Vegas et al. | |
| 10,189,802 B2 | 1/2019 | Mahon et al. | |
| 10,844,028 B2 | 11/2020 | Mahon et al. | |
| 2010/0331234 A1 | 12/2010 | Mahon et al. | |
| 2011/0293703 A1 | 12/2011 | Mahon et al. | |
| 2014/0161830 A1 | 6/2014 | Anderson et al. | |
| 2014/0322309 A1 | 10/2014 | Vegas et al. | |
| 2015/0203439 A1 | 7/2015 | Mahon et al. | |
| 2016/0114042 A1 | 4/2016 | Anderson et al. | |
| 2017/0081667 A1 | 3/2017 | Chen et al. | |
| 2017/0152213 A1 | 6/2017 | Anderson et al. | |
| 2017/0204075 A1 | 7/2017 | Mahon et al. | |
| 2019/0177289 A1 | 6/2019 | Mahon et al. | |

FOREIGN PATENT DOCUMENTS

| | | |
|---|---|---|
| WO | 9428152 A1 | 12/1994 |
| WO | 9502697 A1 | 1/1995 |
| WO | 9516772 A1 | 6/1995 |
| WO | 9534671 A1 | 12/1995 |
| WO | 9622378 A1 | 7/1996 |
| WO | 9712986 A2 | 4/1997 |
| WO | 9721826 A2 | 6/1997 |
| WO | 03022311 A1 | 3/2003 |

OTHER PUBLICATIONS

Gatti "Janus kinase inhibitors and coronavirus disease (COVID)-19: rationale, clinical evidence and safety issues." Pharmaceuticals 14.8 (2021): 738.*
Seavey et al. "The many faces of Janus kinase." Biochemical pharmacology 83.9 (2012): 1136-1145).*
Antisense LNA® GapmeRs Handbook, Oct. 2017, pp. 1-18.
Bertero et al., "Systems-level regulation of microRNA networks by miR-130/301 promotes pulmonary hypertension," The Journal of Clinical Investigation, Aug. 2014, pp. 3514-3528, vol. 124, No. 8.
Bertero et al., "Vascular Stiffness mechanoactivates YAP/TAZ-dependent glutaminolysis to drive pulmonary hypertension," The Journal of Clinical Investigation, Sep. 2016, pp. 3313-3335, vol. 126, No. 9.
Chan et al., "V3 Recombinants Indicate a Central Role for CCR5 as a Coreceptor in Tissue Infection by Human Immunodeficiency Virus Type 1," Journal of Virology, Mar. 1999, pp. 2350-2358, vol. 73, No. 3.
Chan et al., "Differential induction of cellular detachment by envelope glycoproteins of Marburg and Ebola (Zaire) viruses," Journal of General Virology, 2000, pp. 2155-2159, vol. 81.
Chan et al., "Distinct Mechanisms of Entry by Envelope Glycoproteins of Marburg and Ebola (Zaire) Viruses," Journal of Virology, May 2000, pp. 4933-4937, vol. 74, No. 10.
Chan et al., "Folate Receptor-α Is a Cofactor for Cellular Entry by Marburg and Ebola Viruses," Cell Press, Jul. 13, 2001, pp. 117-126, vol. 106.

(Continued)

*Primary Examiner* — Kimberly Chong
(74) *Attorney, Agent, or Firm* — The Webb Law Firm

(57) ABSTRACT

Provided herein are methods of treating a coronavirus infection in a patient, comprising administering an agent to the patient in an amount effective to increase cellular lysosomal pH in cells of the patient. As provided herein, the agent is one or more of an agent for reducing expression or activity of nuclear receptor coactivator 7 (NCOA7) in the patient, an RNAi agent or antisense reagent for knocking down expression of a v-rel avian reticuloendotheliosis viral oncogene homolog A (RelA/p65) transcript, or a janus kinase (JAK) inhibitor, thereby increasing cellular lysosomal pH in cells of the patient.

19 Claims, 9 Drawing Sheets
(1 of 9 Drawing Sheet(s) Filed in Color)
Specification includes a Sequence Listing.

(56) References Cited

OTHER PUBLICATIONS

Chen et al., "Epidemiological and clinical characteristics of 99 cases of 2019 novel coronavirus pneumonia in Wuhan, China: a descriptive study," Lancet, Jan. 29, 2020, pp. 507-513, vol. 395.
Clerkin et al., "COVID-19 and Cardiovascular Disease," Circulation, May 19, 2020, pp. 1648-1655, vol. 141.
Corey, "Chemical modification: the key to clinical application of RNA interference?" The Journal of Clinical Investigation, Dec. 2007, pp. 3615-3622, vol. 117, No. 12.
Doyle et al., "The interferon-inducible isoform of NCOA7 inhibits endosome-mediated viral entry," nature microbiology, Dec. 2018, pp. 1369-1376, vol. 3.
Furumoto et al., "The arrival of JAK inhibitors: advancing the treatment of immune and hematologic disorders," NIH Public Access, Oct. 1, 2014, pp. 1-12.
Hamming et al., "Tissue Distribution of ACE2 protein, the functional receptor for SARS coronavirus. A first step in understanding SARS pathogenesis," Journal of Pathology, 2004, pp. 631-637, vol. 203.
Harrison et al., "Momelotinib versus best available therapy in patients with myelofibrosis previously treated with ruxolitinib (Simplify 2): a randomised, open-label, phase 3 trial," Lancet, Feb. 2018, pp. 73-81, vol. 5.
Herold, "Overexpression of the Interferon-Inducible Isoform 4 of NCOA7 Dissects the Entry Route of Enveloped Viruses and Demonstrates that HIV Enters Cells via Fusion at the Plasma Membrane," Viruses, Jan. 29, 2019, pp. 1-4, vol. 11, No. 121.
Hoffmann et al., "SARS-CoV-2 Cell Entry Depends on ACE2 and TMPRSS2 and Is Blocked by a Clinically Proven Protease Inhibitor," Cell Press, Apr. 16, 2020, pp. 1-19, vol. 181.
Hu et al., "Therapeutic siRNA: state of the art," Signal Transduction and Targeted Therapy, Jun. 19, 2020, pp. 1-25, vol. 5, No. 101.
Lima et al., "Single-Stranded siRNAs Activate RNAi in Animals," Cell Press, Aug. 31, 2012, pp. 1-23, vol. 150.
Litvak et al., "Role of the transcription factor C/EBPδ in a regulatory circuit that discriminates between transient and persistent Toll-like receptor 4 induced signals," HHS Public Access, 2009, pp. 1-17, PMC.
Madjid et al., "Potential Effects of Coronaviruses on the Cardiovascular System: A Review," JAMA Cardiology, Jul. 2020, pp. 831-840, vol. 5, No. 7.
Mesa et al., "Simplify-1: A Phase III Randomized Trial of Momelotinib Versus Ruxolitinib in Janus Kinase Inhibitor—Naïve Patients With Myelofibrosis," Journal of Clinical Oncology, Dec. 1, 2017, pp. 1-10, vol. 35, No. 34.
Ou et al., "Characterization of spike glycoprotein of SARS-CoV-2 on virus entry and its immune cross-reactivity with SARS-CoV," Nature Communications, 2020, pp. 1-12, vol. 11.
Peruzzi et al., "A novel Chimpanzee serotype-based adenoviral vector as delivery tool for cancer vaccines," Vaccine, Jan. 20, 2009, pp. 1293-1300, vol. 27.
Quemener et al., "The powerful worid of antisense oligonucleotides: From bench to bedside," Wiley Interdisciplinry Reviews: RNA, Feb. 26, 2020, pp. 1-22, vol. 11.
Sabnis et al., "A Novel Amino Lipid Series for mRNA Delivery: Improved Endosomal Escape and Sustained Pharmacology and Safety in Non-human Primates," Molecular Therapy, Jun. 2018, pp. 1509-1519, vol. 26, No. 6.
Shen et al., "Survey and Summary: Chemistry, mechanism and clinical status of antisense oligonucleotides and duplex RNAs," Nucleic Acids Research, Dec. 12, 2017, pp. 1584-1600, vol. 46, No. 4.
Shi et al., "Induced pluripotent stem cell technology: a decade of progress," HHS Public Access, Mar. 14, 2019, pp. 1-39.
Tuschl, "Expanding small RNA interference," Nature Biotechnology, May 2002, pp. 446-448, vol. 20.
Watts et al., "Gene silencing by siRNAs and antisense oligonucleotides in the laboratory and the clinic," NIH Public Access, Feb. 7, 2014, pp. 1-28, PMC.
Whitehead et al., "Degradable Lipid Nanoparticles with Predictable In Vivo siR Delivery Activity," HHS Public Access, 2014, pp. 1-22, Nat Commun.
Wienerroither et al., "Cooperative Transcriptional Activation of Antimicrobial Genes by STAT and NF-kB Pathways by Concerted Recruitment of the Mediator Complex," Cell Reports, Jul. 14, 2015, pp. 300-312, vol. 12.
Wu et al., "Improved siRNA/shRNA Functionality by Mismatched Duplex," PLoS ONE, Dec. 9, 2011, pp. 1-9, vol. 6, Is. 12.
Wu et al., "Modelling diastolic dysfunction in induced pluripotent stem cell-derived cardiomyocytes from hypertrophic cardiomyopathy patients," European Heart Journal, Jun. 20, 2019, pp. 3685-3695a, vol. 40.
Yan et al., "Structural basis for the recognition of SARS-CoV-2 by full-length human ACE2," Science, Mar. 4, 2020, pp. 1444-1448, vol. 367.
Yonezawa et al., "Recent advances in siRNA delivery mediated by lipid-based nanoparticles," Advanced Drug Delivery Reviews, Aug. 6, 2020, pp. 64-78, vol. 154-155.
Yu et al., "BolA (BolA Family Member 3) Deficiency Controls Endothelial Metabolism and Glycine Homeostasis in Pulmonary Hypertension," Circulation, May 7, 2019, pp. 2238-2255, vol. 139.
Zhang et al., "AMP-activated Protein Kinase Phosphorylation of Angiotensin-Converting Enzyme 2 in Endothelium Mitigates Pulmonary Hypertension," American Journal of Respiratory and Critical Care Medicine, Aug. 15, 2018, pp. 509-520, vol. 198, Is. 4.
Zhou et al., "COVID-19: a recommendation to examine the effect of hydroxychloroquine in preventing infection and progression," Journal of Antimicrobial Chemotherapy, Mar. 20, 2020, pp. 1667-1670, vol. 75.

\* cited by examiner

TGGTAAAAGCCAGGTTGAAGTGGAAAGGAAGGGCATGTGTCTAGTTTATGCCT
CTTTATCCAGCTTGATCTGTGTCTTCAAATATATAGCAGGATAGGGA[C/G]T
CCATAGTCATGTCCCTGAATGGGAAGACACCTCCTGGCCAGTATCCTTGCCAA
GGTAAACACTGTCAAATGATCATTTCTTGGTTTAGAATAGCAAAT

*FIG. 5*

Homo sapiens nuclear receptor coactivator 7 (NCOA7), transcript variant 6, mRNA

NCBI Reference Sequence: NM_001199622.2

```
>NM_001199622.2 Homo sapiens nuclear receptor coactivator 7 (NCOA7),
transcript variant 6, mRNA
AGTTGTAGCTCAGCGTGGCTACAAGTAACTGTGGTGTGGAAGCAGAGTAGAGAGAAAACTTGTTCCTCAT
TAGAGAGAGAGCCACACTTCTCACTGCTCACAATGAGAGGCCAAAGATTACCCTTGGACATCCAGATTTT
CTATTGTGCCAGACCTGACGAAGAGCCTTTTGTGAAGATCATCACTGTTGAAGAGGCAAAGCGCAGGAAG
AGCACATGCAGCTACTATGAAGACGAGGACGAAGAGGTGCTGCCTGTCCTACGGCCCCACAGCGCGCTCC
TGGAGAATATGCACATCGAGCAGCTGGCCCGACGCCTTCCTGCAAGGGTGCAAGGGTATCCATGGAGACT
GGCCTATAGCACGTTAGAGCACGGGACCAGCTTAAAGACGCTCTACCGGAAATCGGCATCACTAGACAGT
CCTGTCCTATTGGTCATCAAAGATATGGATAATCAGATTTTTGGAGCATATGCAACTCATCCTTTCAAGT
TCAGTGACCACTATTATGGCACAGGCGAAACTTTTCTCTACACATTCAGCCCTCATTTTAAGGTCTTTAA
GTGGAGTGGAGAAAATTCATACTTTATCAATGGAGACATAAGTTCTTTAGAACTTGGTGGTGGAGGGGGA
CGATTTGGTTTATGGCTAGATGCTGATTTATACCACGGACGAAGCAACTCTTGCAGCACTTTCAATAATG
ATATTCTTTCCAAAAAGGAAGACTTCATAGTTCAGGATCTGGAGGTGTGGGCATTTGATTGAAATTCAGA
CTGCCTTAAAATATAACATTAAAAAGACTGGGTTCGATCAGCCCTCCTAAAGCTGGCTGGAAAAAGAAGC
CCCAGCCCAGCCTGCCTCATCCCACCCCAATGCTTCCTTTCTGCCATCATCTCAGAGCATGATCACATTG
CAGAAAGATTCTGGAAGGTCCATGTAGAGGGCAGACATTGAAGAAAGAAACTTAAAATCCAGGTTGTTGA
AAAGACTTTGTACTCCCACTTCCTCCAAATCCATACAGTGAGGAATCAGAGTGTTTATAGATATATGAGT
TGAATGCAATTTTTATTTTTGGTAACTGTGAAAAATAAGATACTGTGGATATATACATGCCTTGTGTATT
TATCAGCATAATTTTCATTACCAAAATGTACAGCTATTATTTGCCATGGAAAAGGTTAGTCTCATTTAGA
AAAATCGAAAGTGCACAGCACTTAAAGGGAATATATGAGGTTTTTTTTTTTAAAAAAAAACTTTTATT
TATTATTTGTAGTATATTGTCTGAAATGTGTCGGCAGTTTTTTTCTTTAATGTGTCAAATCTTGAAAT
ATTAAATGTATACATTTTGTGCTATGTTTGGGAACAAATCTGTTTGATTTATATAGTTTTATATTGAAT
TTTTTTTGCCCTGATTGTTTAGGGTGATAGGTCTTAAGCAGCATATATCTATATATCTGTATGTGGGTAT
ATAGAGATATATGTGTGTGTGTATGTATATGTACATATACATATATATGAGTGTATAATTCTAAATTTCT
AAAAACTCATTATGAATGTTCATCAATTTGACTATTATAGGCCAGCTTTCCATTTAGTCAATAAAAGCGT
ACATTTTAGTTACTTACCTTGAACATATTCGTGTGAAAAAGAATACATCATTTCTCACAGTCTTAAGTT
GATATTTATAGAAATGAATACCTTTGTGAACCTAGACTTAGAACAAATCCTGCTTTTGAAAAAAAATGTT
TTGCTTCTTACAAAATCATTTGTGTTAATAACAAAAACTTTATTTTCGGAGTGTTCTTTGTATAACTTTT
CCAAGCTTTTACATTAACGAGCAGGCCTCTGTCTTAAAAGGGACTCAGTATATTAATTTCTGCATTTTTT
AAATCAAATGAAAAACGTCAAATTGGACCAATTGTCTTGGTTTCTTGATTCATTTATTTGAGAAAAAAAC
AATACAAAGAAATGCATTCATATCAAAATTGGAATAGAAAGGAAAACCTATTTTTAAGATATCAACCTAT
TTTCACATCATAAAACATCTATTACATAAAATAAAGGTCCAGGCATAGTGGCTCTTGCCTGTAATCCCAG
CACTTTGGGAGGCCGAGGCAGGTGGATCACTCAAGGTCACAAGTTTGAGACCAGTCTGGCCAACATGGTG
AAACCCCATCTCTACTAAAAGTACAAATATTAGCCGACTATGTGGCGGGCACCTGTAATCCCACCTACTC
GGGAGGCTGAGGCAGGAGAATTGCTTGAATCCGGGAAGCAGAGGTTGTAGTGAGCCAAGATCGTGCCACT
GCACTCTATCCTGGGTAACAGCGAGACTCTGTCTTAAAAATAATAACAATAATAATAATAATAAAGACTT
```

FIG. 7-1

(sequence continued from Fig. 7-1)

ACTTAACCAATATTATTGATTACCAGACTTTTATGAAAGCCAAAGACTGCTTGCTAGTAGGAAAAAATTT
CAAATAATAACCAAAGCTGAAAAATGGTCTGTCATAAATTATTTCCCCGGTAATTTTTGAAAGGAAAAAT
GTATAACAAGTACTATTTACATATCTGCATTTAAAAAGCAATTCTTAGAATACTTCCTTTACATTATTC
TCCTATTTTAGACATTTGTGAAAGAGAACAAATTGTCCAGTGGCCTCCTGTCAGATCAACAATTATTAT
ACTCCTTAATTCCATGCAAATTTAAATGAATGCTATAAAATTTTAAATCTGTAGCCTGGGTGTACGTTTC
ACTCAAGTTCTCCTACTGAGGACTCTTGACTAACAGCATACTGGCAGTTTCACCTTAACCTGCTCGTTAA
ATAATGTGTTGGTGTGAGATATCAGGAATGTCTCATGATATCACGTTTACCATTTACACCATCTGCAACC
ATATGCTATTAATAAAATGGAAAAAAACAAAATGGTCATTTGCATATACTTCACTCTGACCTAGTTTAG
TCCATGATACTATAATTGTGAGAGCATATCCAGATGCTGTGTTCTCTATGTAAACAGTATTGTCCATTC
AGAAATGTGTGACCCTTCATTTATGGATATTGACTATATGTAATGCAGTGCTATCCCAATATTTTCAATA
AAGGACTTTATGCATTCAGTGATTTTCTTTCCCAAAGATTCATTCATCAGGTATTTACTGGGTACCAGAG
TGTTTATTTTTGTGAGAGGATGGTGAAATATCCAAGACTAAACAAGGTCCAGAGCTCATGTTTTCACTGC
TGCCCTGGAAACTCCCTCTTCATTCCCTGTAGCCACCCTCCTAATTGTCTCATCAGTTCACGGAAACTGC
TCTCATTATGGTTACCAGAGACAACTCTTGGCTGTATCTACCAGTCTCTTCTAATCTTTCTAGCTGTGCA
ATGAATGACAACCTCCTCCTCTTAACATCTGTCTTAACCTACTTCATAATTTCCGTAAGGGACACTTTAC
TCTCTGATAAATTTTCTTTGGCATCCTGACACCTAGCCCCTAGATGTTGGGCTAGATGAAGACCCCAAGC
AGTCTTCATTGCTTCATAATTCCTCAGTTCATAAGTCCATATCAAAGGACTTGGGTGGGAGGAGGCAACC
AAATGTTTCTTCAGACTCTACTGAAAATGATTAGATGCATCCCCGTGCTACAAGCCACCAGAGACATCCT
GCACTATTATAAGTATGTCTTCCCTTAATTTGATCTCCCTCTCCTTGATGCCTTTTAAAGTTTTAGAGAC
ACATTGATATGGTTTGGCTGTGTGTCCCCACCAACATCTCATTGGAATTATAATCCCCACATGTTGAGGG
AGGGACCTAGTGGGATGTGATTAGAACATGGGGGCGGTTTCCCCCATGCTGTTCTCATGATAGTGAGGGA
GTTTTCATGAGATCTGTTTTAAAATGTTTGGCAGTTCCACCCTCACCCTCTCTTCTGCTGCCATGTAAGA
TGTGCCTTGCTTCCCCTTTGCCTTCTGCCATGATTGTAAATTTCCTGACGCCTACCCAGCCATGTGAAAC
TGTGAGTCCATTAAACCTCTTTTCTTTATAAATAA

FIG. 7-2

Homo sapiens RELA proto-oncogene, NF-kB subunit (RELA), transcript variant 2, mRNA NCBI Reference Sequence: NM_001145138.1

```
   1 agcgcgcagg cgcggccgga ttccgggcag tgacgcgacg gcggccgcg cggcgcattt
  61 ccgcctctgg cgaatggctc gtctgtagtg cacgccgcgg gcccagctgc gaccccggcc
 121 ccgccccgg gaccccggcc atggacgaac tgttcccct catcttcccg gcagagccag
 181 cccaggcctc tggcccctat gtggagatca ttgagcagcc caagcagcgg ggcatgcgct
 241 tccgctacaa gtgcgagggg cgctccgcgg gcagcatccc aggcgagagg agcacagata
 301 ccaccaagac ccaccccacc atcaagatca atggctacac aggaccaggg acagtgcgca
 361 tctccctggt caccaaggac cctcctcacc ggcctcaccc ccacgagctt gtaggaaagg
 421 actgccggga tggcttctat gaggctgagc tctgccgga ccgctgcatc cacagtttcc
 481 agaacctggg aatccagtgt gtgaagaagc gggacctgga gcaggctatc agtcagcgca
 541 tccagaccaa caacaacccc ttccaagaag agcagcgtgg ggactacgac ctgaatgctg
 601 tgcggctctg cttccaggtg acagtgcggg acccatcagg caggccctc cgcctgccgc
 661 ctgtcctttc tcatcccatc tttgacaatc gtgcccccaa cactgccgag ctcaagatct
 721 gccgagtgaa ccgaaactct ggcagctgcc tcggtgggga tgagatcttc ctactgtgtg
 781 acaaggtgca gaaagaggac attgaggtgt atttcacggg accaggctgg gaggcccgag
 841 gctccttttc gcaagctgat gtgcaccgac aagtggccat tgtgttccgg acccctccct
 901 acgcagaccc cagcctgcag gctcctgtgc gtgtctccat gcagctgcgg cggccttccg
 961 accgggagct cagtgagccc atggaattcc agtacctgcc agatacagac gatcgtcacc
1021 ggattgagga gaaacgtaaa aggacatatg agaccttcaa gagcatcatg aagaagagtc
1081 cttttcagcg g acccaccgac ccccggcctc cacctcgacg cattgctgtg ccttcccgca
1141 gctcagcttc tgtccccaag ccagcacccc agccctatcc ctttacgtca tccctgagca
1201 ccatcaacta tgatgagttt cccaccatgg tgttccttc tgggcagatc agccaggcct
1261 cggccttggc cccggcccct cccaagtcc tgcccaggc tccagcccct gccctgctc
1321 cagccatggt atcagctctg gccaggccc agcccctgt cccagtccta gccccaggcc
1381 ctcctcaggc tgtggcccca cctgccccca gcccaccca ggctggggaa ggaacgctgt
1441 cagaggccct gctgcagctg cagtttgatg atgaagacct ggggccttg cttggcaaca
1501 gcacagaccc agctgtgttc acagacctgg catccgtcga caactccgag tttcagcagc
1561 tgctgaacca gggcatacct gtggccccc acacaactga gccatgctg atggagtacc
1621 ctgaggctat aactcgccta gtgacagggg cccagaggcc cccgaccca gctcctgctc
1681 cactggggc cccggggctc cccaatggcc tctttcagg agatgaagac ttctcctcca
1741 ttgcggacat ggacttctca gccctgctga gtcagatcag ctcctaaggg ggtgacgcct
1801 gccctcccca gagcactggg ttgcaggga ttgaagccct ccaaaagcac ttacggattc
1861 tggtggggtg tgttccaact gccccaact ttgtggatgt cttccttgga gggggagcc
1921 atattttatt cttttattgt cagtatctgt atctctctct cttttggag gtgcttaagc
1981 agaagcatta acttctctgg aaaggggga gctgggaaa ctcaaacttt tccctgtcc
2041 tgatggtcag ctcccttctc tgtagggaac tctggggtcc cccatcccca tcctccagct
2101 tctggtactc tcctagagac agaagcaggc tggaggtaag gcctttgagc ccacaaagcc
2161 ttatcaagtg tcttccatca tggattcatt acagcttaat caaaataacg ccccagatac
2221 cagcccctgt atggcactgg cattgtccct gtgcctaaca ccagcgtttg agggctggc
2281 cttcctgccc tacagaggtc tctgccggct cttttccttgc tcaaccatgg ctgaaggaaa
2341 ccagtgcaac agcactggct ctctccagga tccagaaggg gtttggtctg ggacttcctt
2401 gctctccctc ttctcaagtg ccttaatagt agggtaagtt gttaagagtg ggggagagca
2461 ggctggcagc tctccagtca ggaggcatag ttttttactga acaatcaaag cacttggact
2521 cttgctcttt ctactctgaa ctaataaatc tgttgccaag ctggctagaa aaaaaaaaa
2581 aaaaaa
```

*FIG. 8*

SEQUENCE LISTING

<160> NUMBER OF SEQ ID NOS: 12

<210> SEQ ID NO 1
<211> LENGTH: 201
<212> TYPE: DNA
<213> ORGANISM: Homo sapiens

<400> SEQUENCE: 1

| | | | | | | |
|---|---|---|---|---|---|---|
| tggtaaaagc | caggttgaag | tggaaaggaa | gggcatgtgt | ctagtttatg | cctctttatc | 60 |
| cagcttgatc | tgtgtcttca | aatatatagc | aggataggga | stccatagtc | atgtccctga | 120 |
| atgggaagac | acctcctggc | cagtatcctt | gccaaggtaa | acactgtcaa | atgatcattt | 180 |
| tcttggttta | gaatagcaaa | t | | | | 201 |

<210> SEQ ID NO 2
<211> LENGTH: 4025
<212> TYPE: DNA
<213> ORGANISM: Homo sapiens

<400> SEQUENCE: 2

| | | | | | | |
|---|---|---|---|---|---|---|
| agttgtagct | cagcgtggct | acaagtaact | gtggtgtgga | agcagagtag | agagaaaact | 60 |
| tgttcctcat | tagagagaga | gccacacttc | tcactgctca | caatgagagg | ccaaagatta | 120 |
| cccttggaca | tccagatttt | ctattgtgcc | agacctgacg | aagagccttt | tgtgaagatc | 180 |
| atcactgttg | aagaggcaaa | gcgcaggaag | agcacatgca | gctactatga | agacgaggac | 240 |
| gaagaggtgc | tgcctgtcct | acggccccac | agcgcgctcc | tggagaatat | gcacatcgag | 300 |
| cagctggccc | gacgccttcc | tgcaagggtg | caagggtatc | catggagact | ggcctatagc | 360 |
| acgttagagc | acgggaccag | cttaaagacg | ctctaccgga | aatcggcatc | actagacagt | 420 |
| cctgtcctat | tggtcatcaa | agatatggat | aatcagattt | ttggagcata | tgcaactcat | 480 |
| cctttcaagt | tcagtgacca | ctattatggc | acaggcgaaa | cttttctcta | cacattcagc | 540 |
| cctcatttta | aggtctttaa | gtggagtgga | gaaaattcat | actttatcaa | tggagacata | 600 |
| agttctttag | aacttggtgg | tgaggggga | cgatttggtt | tatggctaga | tgctgattta | 660 |
| taccacggac | gaagcaactc | ttgcagcact | ttcaataatg | atattctttc | caaaaaggaa | 720 |
| gacttcatag | ttcaggatct | ggaggtgtgg | gcatttgatt | gaaattcaga | ctgccttaaa | 780 |
| atataacatt | aaaaagactg | ggttcgatca | gccctcctaa | agctggctgg | aaaaagaagc | 840 |
| cccagcccag | cctgcctcat | cccaccccaa | tgcttccttt | ctgccatcat | ctcagagcat | 900 |
| gatcacattg | cagaaagatt | ctggaaggtc | catgtagagg | gcagacattg | aagaaagaaa | 960 |
| cttaaaatcc | aggttgttga | aaagactttg | tactcccact | tcctccaaat | ccatacagtg | 1020 |
| aggaatcaga | gtgtttatag | atatatgagt | tgaatgcaat | tttatttt | ggtaactgtg | 1080 |
| aaaaataaga | tactgtggat | atatacatgc | cttgtgtatt | tatcagcata | attttcatta | 1140 |
| ccaaaatgta | cagctattat | ttgccatgga | aaaggttagt | ctcatttaga | aaaatcgaaa | 1200 |
| gtgcacagca | cttaaaggga | atatatgagg | tttttttt | tttaaaaaaa | aacttttatt | 1260 |
| tattatttgt | agtatattgt | ctgaaatgtg | tcggcagttt | ttttctttt | aatgtgtcaa | 1320 |
| atcttgaaat | attaaatgta | tacattttgt | gctatgtttt | gggaacaaat | ctgtttgatt | 1380 |
| tatatagttt | tatattgaat | ttttttgcc | ctgattgttt | agggtgatag | gtcttaagca | 1440 |
| gcatatatct | atatatctgt | atgtgggtat | atagagatat | atgtgtgtgt | gtatgtatat | 1500 |
| gtacatatac | atatatatga | gtgtataatt | ctaaattct | aaaaactcat | tatgaatgtt | 1560 |
| catcaatttg | actattatag | gccagctttc | catttagtca | ataaaagcgt | acattttag | 1620 |

```
ttacttacct tgaacatatt cgtgtgaaaa agaatacatc atttctcaca gtcttaagtt    1680
gatatttata gaaatgaata cctttgtgaa cctagactta gaacaaatcc tgcttttgaa    1740
aaaaaatgtt ttgcttctta caaaatcatt tgtgttaata acaaaaactt tattttcgga    1800
gtgttctttg tataactttt ccaagctttt acattaacga gcaggcctct gtcttaaaag    1860
ggactcagta tattaatttc tgcatttttt aaatcaaatg aaaaacgtca aattggacca    1920
attgtcttgg tttcttgatt catttatttg agaaaaaaac aatacaaaga aatgcattca    1980
tatcaaaatt ggaatagaaa ggaaaaccta tttttaagat atcaacctat tttcacatca    2040
taaaacatct attacataaa ataaaggtcc aggcatagtg gctcttgcct gtaatcccag    2100
cactttggga ggccgaggca ggtggatcac tcaaggtcac aagtttgaga ccagtctggc    2160
caacatggtg aaaccccatc tctactaaaa gtacaaatat tagccgacta tgtggcgggc    2220
acctgtaatc ccacctactc gggaggctga ggcaggagaa ttgcttgaat ccgggaagca    2280
gaggttgtag tgagccaaga tcgtgccact gcactctatc ctgggtaaca gcgagactct    2340
gtcttaaaaa taataacaat aataataata ataaagactt acttaaccaa tattattgat    2400
taccagactt ttatgaaagc caagactgc ttgctagtag gaaaaaattt caaataataa    2460
ccaaagctga aaaatggtct gtcataaatt atttccccgg taatttttga aggaaaaat    2520 gtataacaag tactatttac atatctgcat ttaaaaaagc aattcttaga atacttcctt    2580
tacattattc tcctatttta gacattttgt gaaagagaac aaattgtcca gtggcctcct    2640
gtcagatcaa caattattat actccttaat tccatgcaaa tttaaatgaa tgctataaaa    2700
ttttaaatct gtagcctggg tgtacgtttc actcaagttc tcctactgag gactcttgac    2760
taacagcata ctggcagttt caccttaacc tgctcgttaa ataatgtgtt ggtgtgagat    2820
atcaggaatg tctcatgata tcacgtttac catttacacc atctgcaacc atatgctatt    2880
aataaaatgg aaaaaaacaa aatggtcatt ttgcatatac ttcactctga cctagtttag    2940
tccatgatac tataattgtg agagcatatc cagatgctgt gttctctatg taaaacagta    3000
ttgtccattc agaaatgtgt gacccttcat ttatggatat tgactatatg taatgcagtg    3060
ctatcccaat attttcaata aaggacttta tgcattcagt gatttctttt cccaaagatt    3120
cattcatcag gtatttactg ggtaccagag tgtttatttt tgtgagagga tggtgaaata    3180
tccaagacta aacaaggtcc agagctcatg ttttcactgc tgccctggaa actccctctt    3240
cattccctgt agccacccct ctaattgtct catcagttca cggaaactgc tctcattatg    3300
gttaccagag acaactcttg gctgtatcta ccagtctctt ctaatctttc tagctgtgca    3360
atgaatgaca acctcctcct cttaacatct gtcttaacct acttcataat ttccgtaagg    3420
gacactttac tctctgataa attttctttg gcatcctgac acctagcccc tagatgttgg    3480
gctagatgaa gaccccaagc agtcttcatt gcttcataat tcctcagttc ataagtccat    3540
atcaaaggac ttgggtggga ggaggcaacc aaatgtttct tcagactcta ctgaaaatga    3600
ttagatgcat ccccgtgcta caagccacca gagacatcct gcactattat aagtatgtct    3660
tcccttaatt tgatctcect ctccttgatg cctttaaag ttttagagac acattgatat    3720
ggtttggctg tgtgtcccca ccaacatctc attggaatta taatccccac atgttgaggg    3780
agggacctag tgggatgtga ttagaacatg ggggcggttt cccccatgct gttctcatga    3840
tagtgaggga gttttcatga gatctgtttt aaaatgtttg gcagttccac cctcacctc    3900 tcttctgctg ccatgtaaga tgtgccttgc ttcccctttg ccttctgcca tgattgtaaa    3960
```

```
tttcctgacg cctacccagc catgtgaaac tgtgagtcca ttaaacctct tttctttata    4020
aataa                                                                4025

<210> SEQ ID NO 3
<211> LENGTH: 21
<212> TYPE: DNA
<213> ORGANISM: Artificial Sequence
<220> FEATURE:
<223> OTHER INFORMATION: NCOA7 siRNA

<400> SEQUENCE: 3
gtggaagcag agtagagaga a                                              21

<210> SEQ ID NO 4
<211> LENGTH: 21
<212> TYPE: DNA
<213> ORGANISM: Artificial Sequence
<220> FEATURE:
<223> OTHER INFORMATION: NCOA7 siRNA

<400> SEQUENCE: 4
gaagatcatc actgttgaag a                                              21

<210> SEQ ID NO 5
<211> LENGTH: 21
<212> TYPE: DNA
<213> ORGANISM: Artificial Sequence
<220> FEATURE:
<223> OTHER INFORMATION: RELA siRNA

<400> SEQUENCE: 5
gcttctatga ggctgagctc t                                              21

<210> SEQ ID NO 6
<211> LENGTH: 21
<212> TYPE: DNA
<213> ORGANISM: Artificial Sequence
<220> FEATURE:
<223> OTHER INFORMATION: RELA siRNA

<400> SEQUENCE: 6
gcgcatccag accaacaaca a                                              21

<210> SEQ ID NO 7
<211> LENGTH: 6424
<212> TYPE: DNA
<213> ORGANISM: Homo sapiens

<400> SEQUENCE: 7
atgccctgac ggggggcgca gctgcggggc tggcgaggcg tcgcgcgtgg gaagaggcct    60
aagacacccc gactgcggcg gctgcgcaca cccgatccgg acgcgggggcc ccgcgggcgc   120 gcgcctcgga gctcccgcct cctcctcttg ctcctcctcg gcgtacggtc ctcccctgac   180
ccctccttcc acccgccgag aggatgcgct ccccggcgcc cagcagcaga ggccaccgct   240
cccagaaatg catgcgaccg atccccttct cccggacccc aggagccggc gcccccgccc   300
tgtagggtta cgactcactg attaaaaaga gggactttttt caaatacttt gcacttttga   360
ttgtgtatta tggataccaa ggaagagaag aaggaacgga acaaagtta ttttgctcga    420 ctgaaaaaga aaaacaagc caaacaaaat gcagagacag cctcagctgt agctacaagg   480
actcatactg ggaaggaaga taataataca gtagttttag agccagacaa gtgcaacatt   540
gctgtggaag aggaatatat gactgatgag aaaaaaaaga gaaaaagtaa tcagttaaag   600
```

```
gagatcaggc gtacagaact aaagagatat tatagtattg atgacaatca aaacaaaaca    660
catgataaaa aagagaagaa gatggtggtt cagaagcccc atgggactat ggaatacact    720
gctggaaacc aggacaccct aaactccata gcactgaaat ttaacatcac tcccaataaa    780
ttggtggaac tgaataaact tttcacacat actattgttc caggccaggt ccttttttgtg   840 ccagatgcca actctccttc cagtacctta aggctatcat catccagtcc tggtgctact    900
gtctctcctt catcatcaga tgcagaatat gataaattgc ctgatgctga cttagcacga    960
aaggccttga aacccattga aagagtctta tcgtctactt ctgaagaaga tgagccaggt   1020
gtggtgaaat ttttaaaaat gaattgtcga tacttcaccg atggaaaggg tgtggttggc   1080
ggtgttatga tagtgactcc taacaacatc atgtttgacc ctcataaatc tgatcctctg   1140
gttattgaaa atgggtgtga ggagtatggt ctcatctgcc ccatggaaga ggttgtttcc   1200
attgcgctct acaatgacat ttctcacatg aagatcaaag atgccttgcc atcgcctgga   1260
gaatgggaag acctggcttc agaaaaggat atcaacccat tcagtaagtt caaatctatc   1320
aacaaggaaa aacgacagca gaatggagag aaaattatga cttcggattc cagaccaata   1380 gtaccctttgg agaagtccac aggacataca cctacaaagc cctcaggcag ctctgtgtca   1440
gagaaattaa agaaactgga ctcctctagg gagacatccc atggttctcc cacagtgact   1500
aagctcagca aggaaccttc cgacacttct tctgcatttg aatctacagc caaagaaaac   1560
tttctagggg aagatgatga ttttgttgac ttggaagaac tttcttctca aactggtggt   1620
ggaatgcaca aaaagacac cttgaaggag tgccttctc ttgacccaga ggaacgaaag    1680
aaagctgagt cacaaataaa caattctgcc gtggaaatgc aggtgcagtc agccctagcc   1740
tttttgggaa cagagaatga tgttgaactg aaggggcgc tagatttaga aacctgtgag    1800
aagcaagata taatgccaga agtggacaag cagtctggtt cgccagaaag ccgagtagaa   1860
aacacactga acatacatga agatttagat aaagttaaac tcattgaata ttacctgact   1920
aagaacaaag aagggccaca ggtatctgaa aatttgcaga aaacagaatt aagtgatgga   1980
aaaagtattg aaccagggg aatagacatt acccttagta gttctctttc ccaggcgggt   2040
gatcccataa ctgagggcaa taaagagcca gataagacct gggtgaaaaa gggagagccc   2100
ctcccggtaa aactgaactc ttctacagaa gcaaatgtga ttaaagaggc tctagactcc   2160
tctttggaat ctactctgga caacagctgt caaggtgcac aaatggataa taaatctgaa   2220
gttcagttgt ggctgttaaa gagaattcag gtacccattg aagatatact tccttcaaaa   2280
gaagaaaaaa gcaagacccc acccatgttc ctgtgcatca aagtgggaaa accaatgaga   2340
aaatcctttg ccactcacac tgcagccatg gtccagcagt acggcaaacg gagaaagcag   2400
ccagagtact ggtttgctgt tcctcgggag agggtggatc atttgtacac attctttgtt   2460
cagtggtctc ccgatgtcta tggaaaagat gccaaagagc aaggctttgt ggtggtggag   2520
aaggaagaac tgaacatgat tgacaacttc ttcagtgagc aacaaccaa gagctggag    2580 atcatcactg ttgaagaggc aaagcgcagg aagagcacat gcagctacta tgaagacgag   2640
gacgaagagg tgctgcctgt cctacggccc cacagcgcgc tcctggagaa tatgcacatc   2700
gagcagctgg cccgacgcct tcctgcaagg gtgcaagggt atccatggag actggcctat   2760
agcacgttag agcacgggac cagcttaaag acgctctacc ggaaatcggc atcactagac   2820
agtcctgtcc tattggtcat caaagatatg gataatcaga ttttggagc atatgcaact   2880 catccttca agttcagtga ccactattat ggcacaggcg aaacttttct ctacacattc   2940
```

```
agccctcatt ttaaggtctt taagtggagt ggagaaaatt catactttat caatggagac    3000
ataagttctt tagaacttgg tggtggaggg ggacgatttg gtttatggct agatgctgat    3060
ttataccacg gacgaagcaa ctcttgcagc actttcaata atgatattct ttccaaaaag    3120
gaagacttca tagttcagga tctggaggtg tgggcatttg attgaaattc agactgcctt    3180
aaaatataac attaaaaaga ctgggttcga tcagccctcc taaagctggc tggaaaaaga    3240
agccccagcc cagcctgcct catcccaccc caatgcttcc tttctgccat catctcagag    3300
catgatcaca ttgcagaaag attctggaag gtccatgtag agggcagaca ttgaagaaag    3360
aaacttaaaa tccaggttgt tgaaaagact ttgtactccc acttcctcca aatccataca    3420
gtgaggaatc agagtgttta tagatatatg agttgaatgc aattttttatt tttggtaact    3480
gtgaaaaata agatactgtg gatatataca tgccttgtgt atttatcagc ataattttca    3540
ttaccaaaat gtacagctat tatttgccat ggaaaaggtt agtctcattt agaaaaatcg    3600
aaagtgcaca gcacttaaag ggaatatatg aggttttttt ttttttaaaa aaaaacttttt   3660
atttattatt tgtagtatat tgtctgaaat gtgtcggcag ttttttttct tttaatgtgt    3720
caaatcttga atattaaat gtatacattt tgtgctatgt tttgggaaca aatctgtttg      3780
atttatatag ttttatattg aatttttttt gccctgattg tttagggtga taggtcttaa    3840
gcagcatata tctatatatc tgtatgtggg tatatagaga tatatgtgtg tgtgtatgta    3900
tatgtacata tacatatata tgagtgtata attctaaatt tctaaaaact cattatgaat    3960
gttcatcaat ttgactatta taggccagct ttccatttag tcaataaaag cgtacatttt    4020
tagttactta ccttgaacat attcgtgtga aaaagaatac atcatttctc acagtcttaa    4080
gttgatattt atagaaatga ataccttgt gaacctagac ttagaacaaa tcctgctttt     4140
gaaaaaaaat gttttgcttc ttacaaaatc atttgtgtta ataacaaaaa ctttattttc    4200
ggagtgttct ttgtataact tttccaagct tttacattaa cgagcaggcc tctgtcttaa    4260
aagggactca gtatattaat ttctgcattt tttaaatcaa atgaaaaacg tcaaattgga    4320
ccaattgtct tggtttcttg attcatttat ttgagaaaaa acaatacaa agaaatgcat     4380
tcatatcaaa attggaatag aaaggaaaac ctattttttaa gatatcaacc tattttcaca    4440
tcataaaaca tctattacat aaaataaagg tccaggcata gtggctcttg cctgtaatcc    4500
cagcactttg ggaggccgag gcaggtggat cactcaaggt cacaagtttg agaccagtct    4560
ggccaacatg gtgaaacccc atctctacta aaagtacaaa tattagccga ctatgtggcg    4620
ggcacctgta atcccaccta ctcgggaggc tgaggcagga gaattgcttg aatccgggaa    4680
gcagaggttg tagtgagcca agatcgtgcc actgcactct atcctgggta acagcgagac    4740
tctgtcttaa aaataataac aataataata ataataaaga cttacttaac caatattatt    4800
gattaccaga cttttatgaa agccaaagac tgcttgctag taggaaaaaa tttcaaataa    4860
taaccaaagc tgaaaatgg tctgtcataa attatttccc cggtaatttt tgaaaggaaa     4920
aatgtataac aagtactatt tacatatctg catttaaaaa agcaattctt agaatacttc    4980
ctttacatta ttctcctatt ttagacattt tgtgaaagag aacaaattgt ccagtggcct    5040
cctgtcagat caacaattat tatactcctt aattccatgc aaatttaaat gaatgctata    5100
aaattttaaa tctgtagcct gggtgtacgt ttcactcaag ttctcctact gaggactctt    5160
gactaacagc atactggcag tttcacctta acctgctcgt taaataatgt gttggtgtga    5220
gatatcagga atgtctcatg atatcacgtt taccatttac accatctgca accatatgct    5280
attaataaaa tggaaaaaaa caaaatggtc attttgcata tacttcactc tgacctagtt    5340
```

| | |
|---|---|
| tagtccatga tactataatt gtgagagcat atccagatgc tgtgttctct atgtaaaaca | 5400 |
| gtattgtcca ttcagaaatg tgtgaccctt catttatgga tattgactat atgtaatgca | 5460 |
| gtgctatccc aatattttca ataaaggact ttatgcattc agtgattttc tttcccaaag | 5520 |
| attcattcat caggtattta ctgggtacca gagtgtttat ttttgtgaga ggatggtgaa | 5580 |
| atatccaaga ctaaacaagg tccagagctc atgttttcac tgctgccctg aaactccct | 5640 |
| cttcattccc tgtagccacc tcctaattg tctcatcagt tcacggaaac tgctctcatt | 5700 |
| atggttacca gagacaactc ttggctgtat ctaccagtct cttctaatct ttctagctgt | 5760 |
| gcaatgaatg acaacctcct cctcttaaca tctgtcttaa cctacttcat aatttccgta | 5820 |
| agggacactt tactctctga taaattttct ttggcatcct gacacctagc ccctagatgt | 5880 |
| tgggctagat gaagacccca agcagtcttc attgcttcat aattcctcag ttcataagtc | 5940 |
| catatcaaag gacttgggtg ggaggaggca accaaatgtt tcttcagact ctactgaaaa | 6000 |
| tgattagatg catccccgtg ctacaagcca ccagagacat cctgcactat tataagtatg | 6060 |
| tcttccctta atttgatctc cctctccttg atgccttta aagttttaga gacacattga | 6120 |
| tatggtttgg ctgtgtgtcc ccaccaacat ctcattggaa ttataatccc cacatgttga | 6180 |
| gggagggacc tagtgggatg tgattagaac atggggcgg tttcccccat gctgttctca | 6240 |
| tgatagtgag ggagttttca tgagatctgt tttaaaatgt ttggcagttc caccctcacc | 6300 |
| ctctcttctg ctgccatgta agatgtgcct tgcttcccct ttgccttctg ccatgattgt | 6360 |
| aaatttcctg acgcctaccc agccatgtga aactgtgagt ccattaaacc tcttttcttt | 6420 |
| ataa | 6424 |

<210> SEQ ID NO 8
<211> LENGTH: 2586
<212> TYPE: DNA
<213> ORGANISM: Homo sapiens

<400> SEQUENCE: 8

| | |
|---|---|
| agcgcgcagg cgcggccgga ttccgggcag tgacgcgacg gcgggccgcg cggcgcattt | 60 |
| ccgcctctgg cgaatggctc gtctgtagtg cacgccgcgg gccagctgc gaccccggcc | 120 |
| ccgcccccgg gaccccggcc atggacgaac tgttcccct catcttcccg gcagagccag | 180 |
| cccaggcctc tggcccctat gtggagatca ttgagcagcc caagcagcgg ggcatgcgct | 240 |
| tccgctacaa gtgcgagggg cgctccgcgg gcagcatccc aggcgagagg agcacagata | 300 |
| ccaccaagac ccacccacc atcaagatca atggctacac aggaccaggg acagtgcgca | 360 |
| tctccctggt caccaaggac cctcctcacc ggcctcaccc ccacgagctt gtaggaaagg | 420 |
| actgccgga tggcttctat gaggctgagc tctgcccgga ccgctgcatc cacagtttcc | 480 |
| agaacctggg aatccagtgt gtgaagaagc gggacctgga gcaggctatc agtcagcgca | 540 |
| tccagaccaa caacaacccc ttccaagaag agcagcgtgg ggactacgac ctgaatgctg | 600 |
| tgcggctctg cttccaggtg acagtgcggg acccatcagg caggcccctc gcctgccgc | 660 |
| ctgtcctttc tcatcccatc tttgacaatc gtgcccccaa cactgccgag ctcaagatct | 720 |
| gccgagtgaa ccgaaactct ggcagctgcc tcggtgggga tgagatcttc ctactgtgtg | 780 |
| acaaggtgca gaaagaggac attgaggtgt atttcacggg accaggctgg gaggcccgag | 840 |
| gctccttttc gcaagctgat gtgcaccgac aagtggccat tgtgttccgg acccctcct | 900 |
| acgcagaccc cagcctgcag gctcctgtgc gtgtctccat gcagctgcgg cggccttccg | 960 |

-continued

```
accgggagct cagtgagccc atggaattcc agtacctgcc agatacagac gatcgtcacc    1020
ggattgagga gaaacgtaaa aggacatatg agaccttcaa gagcatcatg aagaagagtc    1080
ctttcagcgg acccaccgac ccccggcctc cacctcgacg cattgctgtg ccttcccgca    1140
gctcagcttc tgtccccaag ccagcacccc agccctatcc ctttacgtca tccctgagca    1200
ccatcaacta tgatgagttt cccaccatgg tgtttccttc tgggcagatc agccaggcct    1260
cggccttggc cccggcccct ccccaagtcc tgccccaggc tccagcccct gcccctgctc    1320
cagccatggt atcagctctg gcccaggccc agcccctgt cccagtccta gccccaggcc    1380
ctcctcaggc tgtggcccca cctgccccca agcccaccca ggctggggaa ggaacgctgt    1440
cagaggccct gctgcagctg cagtttgatg atgaagacct gggggccttg cttggcaaca    1500
gcacagaccc agctgtgttc acagacctgg catccgtcga caactccgag tttcagcagc    1560
tgctgaacca gggcatacct gtggcccccc acacaactga gcccatgctg atggagtacc    1620
ctgaggctat aactcgccta gtgacagggg cccagaggcc ccccgaccca gctcctgctc    1680 cactggggc cccggggctc cccaatggcc tcctttcagg agatgaagac ttctcctcca    1740
ttgcggacat ggacttctca gccctgctga gtcagatcag ctcctaaggg ggtgacgcct    1800
gccctcccca gagcactggg ttgcagggga ttgaagccct ccaaaagcac ttacggattc    1860
tggtggggtg tgttccaact gcccccaact ttgtggatgt cttccttgga gggggagcc    1920 atattttatt cttttattgt cagtatctgt atctctctct cttttggag gtgcttaagc    1980 agaagcatta acttctctgg aaggggggga gctggggaaa ctcaaacttt tcccctgtcc    2040
tgatggtcag ctcccttctc tgtagggaac tctggggtcc cccatcccca tcctccagct    2100
tctggtactc tcctagagac agaagcaggc tggaggtaag gcctttgagc ccacaaagcc    2160
ttatcaagtg tcttccatca tggattcatt acagcttaat caaaataacg ccccagatac    2220
cagcccctgt atggcactgg cattgtccct gtgcctaaca ccagcgtttg aggggctggc    2280
cttcctgccc tacagaggtc tctgccggct cttttccttgc tcaaccatgg ctgaaggaaa    2340
ccagtgcaac agcactggct ctctccagga tccagaaggg gtttggtctg ggacttcctt    2400
gctctccctc ttctcaagtg ccttaatagt agggtaagtt gttaagagtg ggggagagca    2460
ggctggcagc tctccagtca ggaggcatag ttttttactga acaatcaaag cacttggact    2520
cttgctcttt ctactctgaa ctaataaatc tgttgccaag ctggctagaa aaaaaaaaa    2580 aaaaaa                                                              2586
```

```
<210> SEQ ID NO 9
<211> LENGTH: 21
<212> TYPE: DNA
<213> ORGANISM: Artificial Sequence
<220> FEATURE:
<223> OTHER INFORMATION: NCOA7 siRNA sense sequence

<400> SEQUENCE: 9
ggaaugucuc augauaucat t                                              21

<210> SEQ ID NO 10
<211> LENGTH: 21
<212> TYPE: DNA
<213> ORGANISM: Artificial Sequence
<220> FEATURE:
<223> OTHER INFORMATION: NCOA7 siRNA anti-sense sequence

<400> SEQUENCE: 10
ugauaucaug agacauucct g                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: RELA siRNA sense sequence

<400> SEQUENCE: 11
cccuuuacgu caucccugat t                                            21

<210> SEQ ID NO 12
<211> LENGTH: 21
<212> TYPE: DNA
<213> ORGANISM: Artificial Sequence
<220> FEATURE:
<223> OTHER INFORMATION: RELA siRNA anti-sense sequence

<400> SEQUENCE: 12
ucagggauga cguaaaggga t                                            21
```

THERAPEUTIC AND DIAGNOSTIC TARGET FOR SARS-COV-2 AND COVID-19

CROSS REFERENCE TO RELATED APPLICATIONS

This application claims the benefit of U.S. Provisional Patent Application No. 63/003,571, filed Apr. 1, 2020, which is incorporated herein by reference in its entirety.

STATEMENT REGARDING FEDERALLY SPONSORED RESEARCH

This invention was made with government support under Grant No. HL138437 awarded by the National Institutes of Health. The government has certain rights in the invention.

SEQUENCE LISTING

The Sequence Listing associated with this application is filed in electronic format via EFS-Web and is hereby incorporated by reference into the specification in its entirety. The name of the text file containing the Sequence Listing is 6527-2101446_ST25.txt. The size of the text file is 19,616 bytes, and the text file was created on Mar. 31, 2021.

Severe acute respiratory syndrome coronavirus 2 (SARS-CoV-2) is a novel coronavirus strain that is highly contagious in the human population, complicated by severe respiratory manifestations and death in a varying percentage of infected individuals. Among those infected, there is a higher prevalence and severity of SARS-CoV-2 disease in persons with co-morbid cardiovascular disease, such as hypertension and diabetes. Furthermore, >7% of patients suffer myocardial and cardiovascular injury from the infection (22% of the critically ill), particularly as disease severity intensifies. Recently, it has been reported that the SARS-CoV-2 spike protein can bind 2 and utilize the angiotensin-converting enzyme 2 (ACE2) receptor for gaining entry to human cells. In addition to pulmonary epithelial, brain, mucosal, and renal cells, cardiomyocytes and vascular endothelial cells express ACE2. However, data regarding direct SARS-CoV-2 infection of any cardiovascular cell type are lacking, and it is unclear whether factors that control viral entry into cardiovascular cells underlie SARS-CoV-2 disease characteristics.

Similar to other enveloped coronaviruses, it is thought that upon binding ACE2, SARS-CoV-2 gains entry via an endosomal encapsulation pathway that depends upon lysosomal acidification for entry. The putative effects of hydroxychloroquine in preventing infection may rely upon such an effect of lysosomal pH. However, the crucial molecules that regulate such lysosomal activity and SARS-CoV-2 entry in cells have not been defined. Identification of such molecules could serve as a crucial foundation for development of novel therapeutic drugs to combat this pandemic. Furthermore, it is possible that functional genetic variants (e.g., single nucleotide polymorphisms or SNPs) in molecules that regulate lysosomal acidification in cells could confer a cellular protection or susceptibility to viral entry and could explain the wide and unexplained variation of disease severity in the global population.

SUMMARY

In one aspect or embodiment of the subject matter disclosed herein, a method of treating a coronavirus infection in a patient is provided. The method comprises administering an agent to the patient in an amount effective to increase cellular lysosomal pH in cells of the patient. In some embodiments, the agent is one or more of an agent for reducing expression or activity of nuclear receptor coactivator 7 (NCOA7) in the patient, an RNAi agent or antisense reagent for knocking down expression of a v-rel avian reticuloendotheliosis viral oncogene homolog A (RelA/p65) transcript, or a janus kinase (JAK) inhibitor, thereby increasing cellular lysosomal pH in cells of the patient.

In another aspect or embodiment, a method of reducing infectivity of a coronavirus infection in a cell is provided. The method comprises administering an agent to the cell in an amount effective to increase cellular lysosomal pH in the cell. In some embodiments, the agent is one or more of an agent for reducing expression or activity of nuclear receptor coactivator 7 (NCOA7) in the cell, an RNAi agent or antisense reagent for knocking down expression of a v-rel avian reticuloendotheliosis viral oncogene homolog A (RelA/p65) transcript, or a janus kinase (JAK) inhibitor, thereby increasing cellular lysosomal pH in the cell.

Various aspects of the present disclosure may be further characterized by one or more of the following clauses:

Clause 1: A method of treating a coronavirus infection in a patient, comprising, administering an agent to the patient in an amount effective to increase cellular lysosomal pH in cells of the patient, wherein the agent is one or more of: an agent for reducing expression or activity of nuclear receptor coactivator 7 (NCOA7) in the patient; an RNAi agent or antisense reagent for knocking down expression of a v-rel avian reticuloendotheliosis viral oncogene homolog A (RelA/p65) transcript; or a janus kinase (JAK) inhibitor, thereby increasing cellular lysosomal pH in cells of the patient.

Clause 2: A method of reducing infectivity of a coronavirus infection in a cell, comprising, administering an agent to the cell in an amount effective to increase cellular lysosomal pH in the cell, wherein the agent is one or more of: an agent for reducing expression or activity of nuclear receptor coactivator 7 (NCOA7) in the cell; an RNAi agent or antisense reagent for knocking down expression of a v-rel avian reticuloendotheliosis viral oncogene homolog A (RelA/p65) transcript; or a janus kinase (JAK) inhibitor, thereby increasing cellular lysosomal pH in the cell.

Clause 3: The method of clause 1 or 2, wherein the agent effective to increase cellular lysosomal pH in cells of the patient is an agent for reducing expression or activity of NCOA7.

Clause 4: The method of any one of clauses 1 to 3, wherein the agent effective to increase cellular lysosomal pH in cells of the patient is an RNAi agent or antisense reagent for knocking down expression of an NCOA7 transcript.

Clause 5: The method of any one of clauses 1 to 4, wherein the agent effective to increase cellular lysosomal pH in cells of the patient is an RNAi agent specific to the NCOA7 transcript comprising one or more of an siRNA, an shRNA, or a combination thereof.

Clause 6: The method of any one of clauses 1 to 5, wherein the agent effective to increase cellular lysosomal pH in cells of the patient is an antisense oligonucleotide (ASO).

Clause 7: The method of any one of clauses 1 to 6, wherein the agent effective to increase cellular lysosomal pH in cells of the patient is an RNAi agent or antisense reagent for knocking down expression of a v-rel avian reticuloendotheliosis viral oncogene homolog A (RelA/p65) transcript.

Clause 8: The method of any one of clauses 1 to 7, wherein the RNAi agent or antisense agent is an siRNA, an shRNA, or a combination thereof, specific to a v-rel avian reticuloendotheliosis viral oncogene homolog A (RelA/p65) transcript.

Clause 9: The method of any one of clauses 1 to 8, wherein the agent effective to increase cellular lysosomal pH in cells of the patient is a janus kinase (JAK) inhibitor.

Clause 10: The method of any one of clauses 1 to 9, wherein the JAK inhibitor is momelotinib.

Clause 11: The method of any one of clauses 1 to 10, further comprising obtaining genetic data for the patient and determining if the patient has one or two alleles for C at rs11154337.

Clause 12: The method of any one of clauses 1 to 11, further comprising determining if the patient has one or two alleles for C at rs11154337.

Clause 13: The method of any one of clauses 1 to 12, wherein the patient has one or two alleles for C at rs11154337.

Clause 14: The method of any one of clauses 1 to 13, wherein treating the coronavirus infection comprises reducing the severity of one or more symptoms of the coronavirus infection.

Clause 15: The method of any one of clauses 1 to 14, wherein the coronavirus infection is one or more of Middle East Respiratory Syndrome Coronavirus (MERS-CoV), Severe Acute Respiratory Syndrome Coronavirus-2 (SARS-CoV-2), or a disease caused thereby, such as Coronavirus Disease 2019 (COVID-19).

Clause 16: The method of any one of clauses 1 to 15, wherein in the coronavirus is SARS-CoV-2.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5: An exemplary nucleic acid sequence (SEQ ID NO: 1).

FIG. 7-1 and FIG. 7-2: An exemplary sequence for human NCOA7 mRNA (SEQ ID NO: 2).

FIG. 8: An exemplary sequence for human RELA mRNA (SEQ ID NO: 8).

DETAILED DESCRIPTION

Figure 1A:
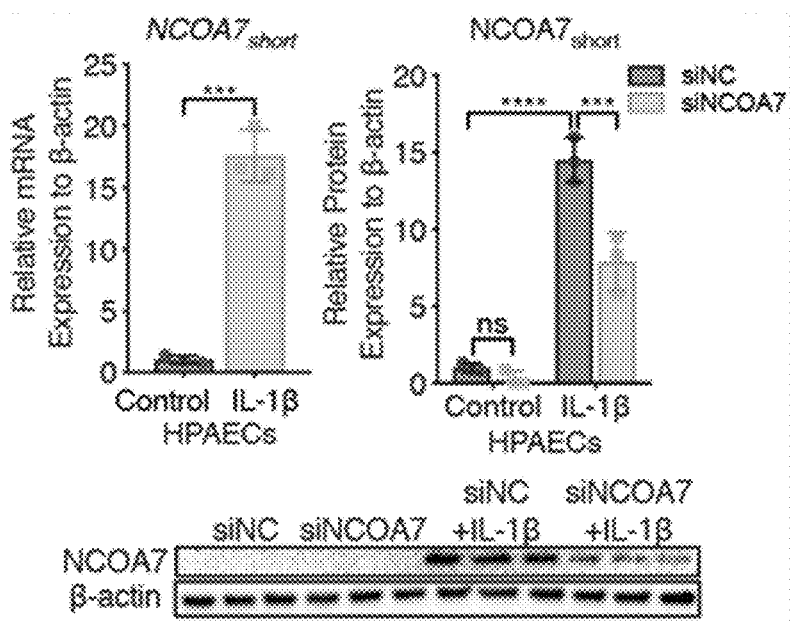
FIGS. 1A and 1B: NCOA7 localizes to the lysosome and induces immune activation of the endothelium. IL-1β upregulates NCOA7 (FIG. 1A) at the lysosome (LAMP1) (FIG. 1B). Statistical analyses were done as Student's t-test. Data are expressed as mean±SD. ns=not significant, $*p<0.05$, $p<0.01$, $*p<0.001$, $****p<0.0001$.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more. Patent publications cited below are hereby incorporated herein by reference in their entirety to the extent of their technical disclosure and consistency with the present specification.

As used herein, the terms "comprising," "comprise" or "comprised," and variations thereof, are open ended and do not exclude the presence of other elements not identified. In contrast, the term "consisting of" and variations thereof is intended to be closed and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of a coronavirus infection means administration to a patient by any suitable dosage regimen, procedure and/or administration route of a composition, device, or structure with the object of achieving a desirable clinical/medical end-point, including but not limited to, for a coronavirus infection, reducing or preventing further development of the coronavirus infection, e.g., as determined below. An amount of any reagent or therapeutic agent, administered by any suitable route, effective to treat a patient is an amount capable of preventing, reducing, and/or eliminating the coronavirus infection and/or reducing the severity of one or more symptoms of the coronavirus infection, for example, fever or chills, cough, shortness of breath or difficulty breathing, fatigue, muscle or body aches, headache, loss of taste or smell, sore throat, congestion or runny nose, nausea or vomiting, or diarrhea.

The therapeutically-effective amount of each therapeutic may range from 1 pg per dose to 10 g per dose, including any amount there between, such as, without limitation, 1 ng, 1 µg, 1 mg, 10 mg, 100 mg, or 1 g per dose. The therapeutic agent may be administered by any effective route, and, for example, as a single dose or bolus, at regular or irregular intervals, in amounts and intervals as dictated by any clinical parameter of a patient, or continuously.

Active ingredients, such as nucleic acids or analogs thereof, may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, intraocular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

Suitable dosage forms may include single-dose, or multiple-dose vials or other containers, such as medical syringes or droppers, containing a composition comprising an active ingredient useful for treatment of a coronavirus infection as described herein.

Pharmaceutical formulations adapted for administration include aqueous and non-aqueous sterile solutions which may contain, for example and without limitation, antioxidants, buffers, bacteriostats, lipids, liposomes, lipid nanoparticles, emulsifiers, suspending agents, and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous solutions and suspensions may be prepared from sterile powders, granules and tablets.

Therapeutic compositions typically must be sterile and stable under the conditions of manufacture and storage. For example, sterile injectable solutions can be prepared by incorporating the active agent in the required amount in an appropriate solvent with one or a combination of ingredients enumerated herein, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single dose or multiple doses, effective to achieve a determinable end-point. The "amount effective" is preferably safe—at least to the extent the benefits of treatment outweighs the detriments, and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single dose or bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc., be proportionally reduced or increased as indicated by the exigencies of the therapeutic situation. In some instances, it may be especially advantageous to formulate compositions in dosage unit form for ease of administration and uniformity of dosage. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

We have been investigating the endothelial cell (EC) pathobiology of the nuclear receptor coactivator 7 (NCOA7). There have been no prior initiatives exploring the relationship of NCOA7 or its functional single nucleotide polymorphism (SNP) rs11154337 (Reference SNP cluster ID) to coronavirus (for example SARS-CoV-2) entry in cells (for example cardiovascular cells). Further, there have been no prior initiatives exploring the therapeutic benefit of modulating NCOA7 and/or diagnostic benefit of screening for its functional SNP rs11154337 to SARS-CoV-2 viral entry in cells. This invention would allow for development of new drugs and repurposing of old drugs for therapy for this pandemic. The inventions would be immediately relevant for development and repurposing of new technologies for therapy as well as for public health initiatives to identify at-risk individuals. This could also be the basis for gene editing therapies of this SNP for prevention of disease.

Coronaviruses are a group of related RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause Middle East Respiratory Syndrome (MERS), Severe Acute Respiratory Syndrome (SARS), or Coronavirus Disease 2019 (COVID-19). In cows and pigs, coronaviruses cause diarrhea, while in mice they cause hepatitis and encephalomyelitis.

SARS-CoV-2 is the virus that causes COVID-19, the respiratory illness responsible for the COVID-19 pandemic. SARS-CoV-2 has been previously referred to by its provisional name, 2019 novel coronavirus (2019-nCoV), and has also been called human coronavirus 2019 (HCoV-19 or hCoV-19). SARS-CoV-2 is a positive-sense single-stranded RNA virus that is contagious in humans. Each SARS-CoV-2 virion is approximately 50-200 nanometres in diameter. SARS-CoV-2 has four structural proteins, known as the S (spike), E (envelope), M (membrane), and N (nucleocapsid) proteins; the N protein holds the RNA genome, and the S, E, and M proteins together create the viral envelope. The spike protein is the protein responsible for allowing the virus to attach to and fuse with the membrane of a host cell; specifically, its S1 subunit catalyzes attachment, the S2 subunit fusion.

Diagnostic tests to detect infection with SARS-CoV-2 may include nucleic acid amplification tests (NAATs) and/or antigen tests.

NAATs, such as real-time reverse transcription-polymerase chain reaction (RT-PCR), are high-sensitivity, high-specificity tests for diagnosing SARS-CoV-2 infection. NAATs detect one or more viral ribonucleic acid (RNA) genes and indicate a current infection or a recent infection but, due to prolonged viral RNA detection, are not always direct evidence for the presence of virus capable of replicating or of being transmitted to others. Most NAATs need to be processed in a laboratory and time to results can vary (~1-3 days), but some NAATs are point-of-care tests with results available in about 15-45 minutes. Most NAATs produce qualitative results.

Antigen tests are immunoassays that detect the presence of a specific viral antigen. Antigen tests generally have similar specificity, but are less sensitive than most NAATs. Most can be processed at the point of care with results available in minutes and thus can be used in screening programs to quickly identify those who are likely to be contagious. Because of the performance characteristics of antigen tests, it may be necessary to confirm some antigen test results (e.g., a negative test in persons with symptoms or a positive test in persons without symptoms) with a laboratory-based NAAT.

Symptoms of SARS-CoV-2 infection may appear 2-14 days after exposure to the virus. Symptoms of SARS-CoV-2 may include, but not limited to, fever or chills, cough, shortness of breath or difficulty breathing, fatigue, muscle or body aches, headache, loss of taste or smell, sore throat, congestion or runny nose, nausea or vomiting, or diarrhea.

Nucleic acids are presented in a 5' to 3' order, and amino acid sequences in an N-terminal to C-terminal order, unless otherwise described.

A "gene" is a sequence of DNA or RNA which codes for a molecule, such as a protein or a functional RNA, such as a non-coding RNA that has a function. Complementary refers to the ability of polynucleotides (nucleic acids) to hybridize to one another, forming inter-strand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). A sequence that specifically hybridizes to another typically has at least 80%, 85%, 90%, 95%, or 99% sequence identity with the other sequence.

Gene expression is the process by which information from a gene is used in the synthesis of a functional gene product, e.g., a protein or functional RNA. Gene expression involves various steps, including transcription, translation, and post-translational modification of a protein, as is broadly-known.

By "expression" or "gene expression," it is meant the overall flow of information from a gene (without limitation, a functional genetic unit for producing a gene product, such as RNA or a protein in a cell, or other expression system encoded on a nucleic acid and comprising: a transcriptional control sequence, such as a promoter and other cis-acting elements, such as transcriptional response elements (TREs) and/or enhancers; an expressed sequence that typically encodes a protein (referred to as an open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence such as TRE or transcription control element, it is meant gene expression from a gene containing the designated sequence operably linked (functionally attached, typically in cis) to the gene. A gene that is "under transcriptional control" of a TRE or transcription control element, is a gene that is transcribed at detectably different levels in the presence of a transcription factor.

A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when factors that regulate transcription, such as DNA-binding proteins, are present or absent—for example an amount of the respective inducer is available to the expression system (e.g., cell), or factors causing suppression of a gene are unavailable or displaced—effective to cause expression of the gene.

Figure 1B:
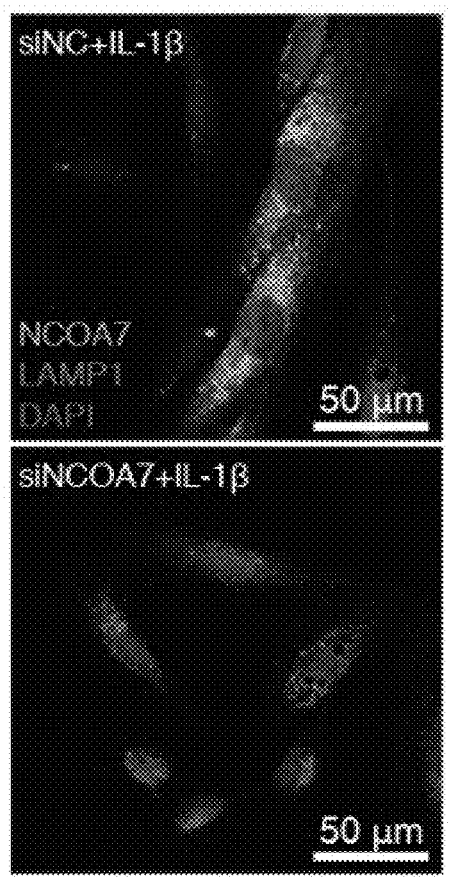
Figure 2A:
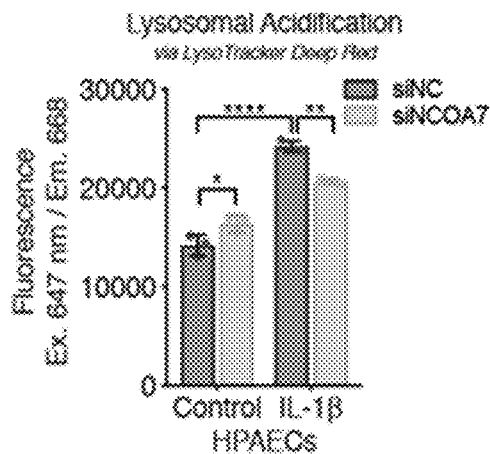
FIGS. 2A-2C: NCOA7 localizes to the lysosome and induces immune activation of the endothelium. Loss of NCOA7 prevents lysosomal acidification (FIG. 2A). Immunoactivation of the endothelium (FIG. 2B) is noted by leukocyte adhesion to an EC monolayer (FIG. 2C). Statistical analyses were done as two-way ANOVA. Data are expressed as mean±SD. ns=not significant, $*p<0.05$, $p<0.01$, $*p<0.001$, $****p<0.0001$.
Figure 2B:
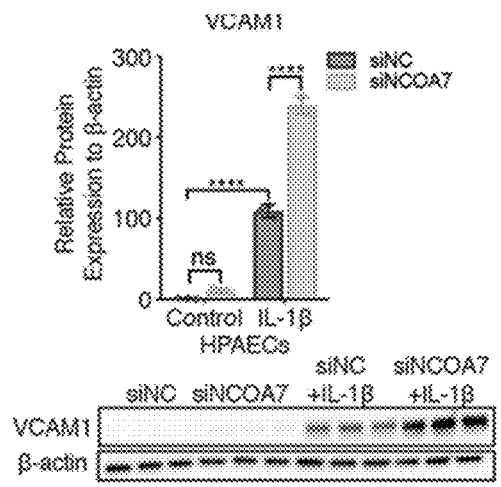
Figure 2C:
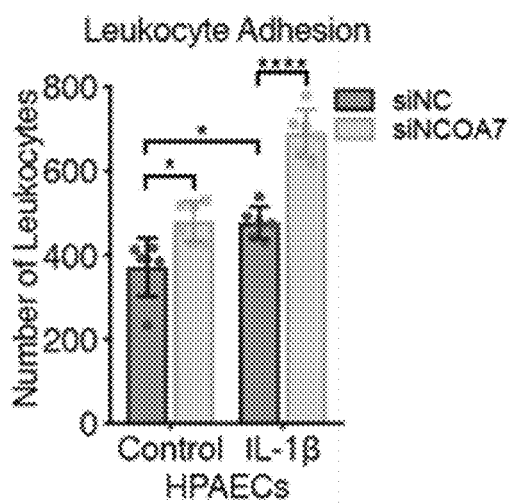
Figure 3A:
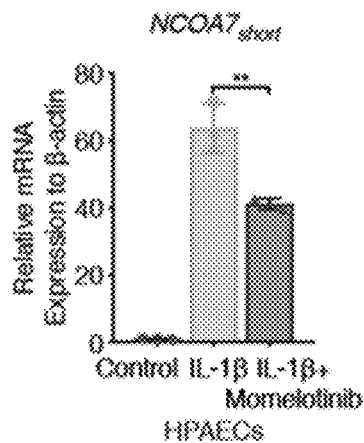
FIGS. 3A-3C: NCOA7 expression is under SNP-dependent control of NF-κB. Treatment with the JAK1/2 inhibitor momelotinib (FIG. 3A) or RNAi of RELA (FIG. 3B) attenuates NCOA7 expression. RelA/p65 binds to NCOA7 promoter (FIG. 3C). Statistical analyses were done as one/two-way ANOVA (FIG. 3A-3B) or Student's t-test (FIG. 3C). Data are expressed as mean±SD. ns=not significant, $*p<0.05$, $p<0.01$, $*p<0.001$, $****p<0.0001$.
Figure 3B:
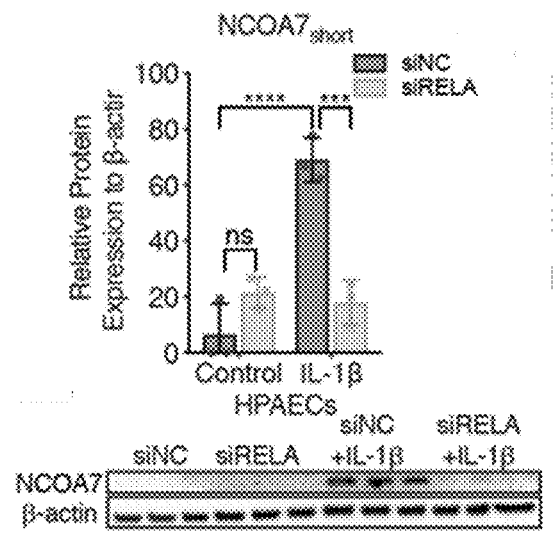
Figure 3C:
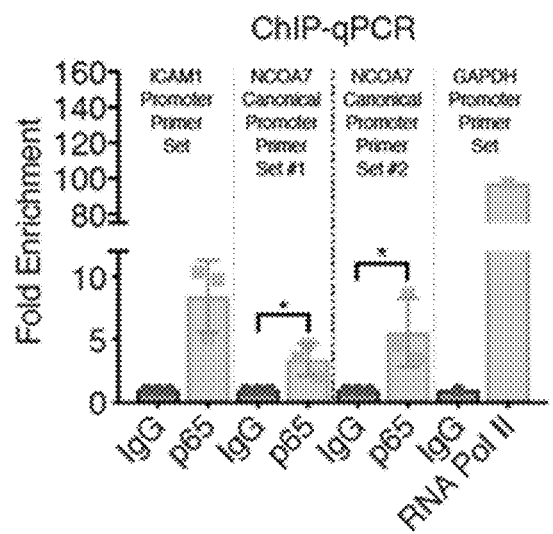
Figure 4A:
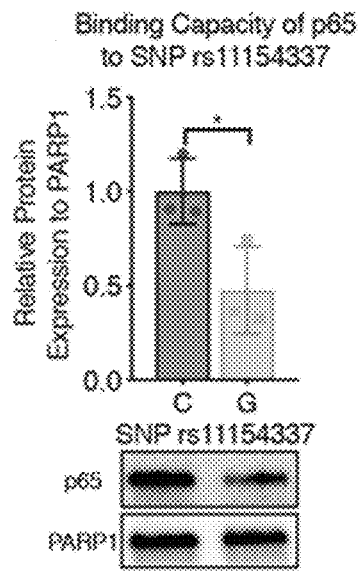
FIGS. 4A-4C: NCOA7 expression is under SNP-dependent control of NF-κB. RelA/p65 binding capacity to the NCOA7 promoter is SNP dependent (FIG. 4A). iPSC-derived ECs (FIG. 4B) show differential NCOA7 expression in control (C/C) versus CRISPR-Cas9-edited (C/G) isogenic lines (FIG. 4C). Statistical analyses were done as Student's t-test (FIG. 4A) or one/two-way ANOVA (FIG. 4C). Data are expressed as mean±SD. ns=not significant, $*p<0.05$, $p<0.01$, $*p<0.001$, $****p<0.0001$.
Figure 4B:
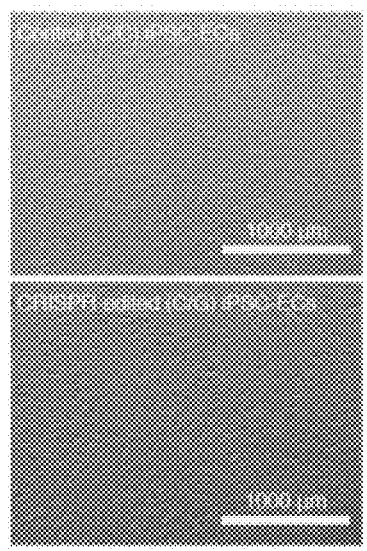
Figure 4C:
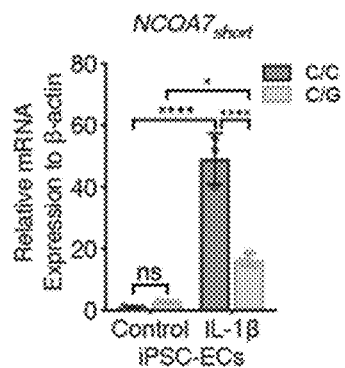
Figure 6:
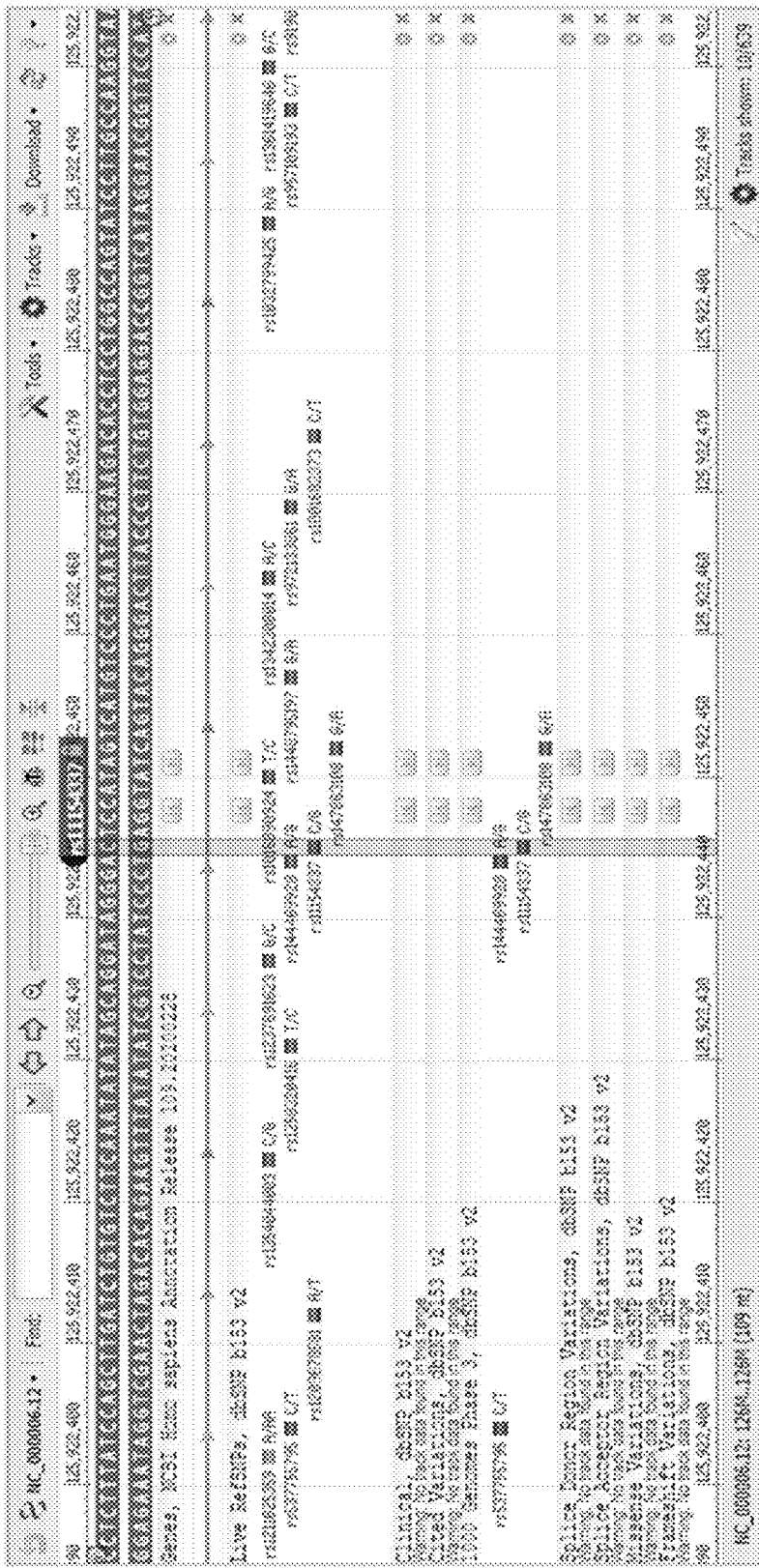
FIG. 6: An exemplary nucleic acid sequence of rs11154337 C allele (top strand).

NCOA7 is the protein product of the NCOA7 gene. An exemplary NCOA7 mRNA sequence (SEQ ID NO: 2) is provided in FIG. 7-1 and FIG. 7-2. The NCOA7 gene has a candidate SNP termed rs11154337 (SEQ ID NO: 1). An exemplary rs11154337 sequence is provided in FIGS. 5-6. rs11154337 is located in the promoter of an interferon-inducible isoform of NCOA7 (NCOA7short) that we first identified in an unpublished genome-wide association study (GWAS) of survival in human pulmonary arterial hypertension. Other mutations or polymorphisms located in the same intron as rs11154337, e.g., as shown in FIG. 6, or in linkage disequilibrium with rs11154337 may either be indicative of a high risk genotype and may functionally affect expression of NCOA7, and therefore may be, like rs11154337 or in combination therewith, useful in detecting persons especially susceptible to coronavirus infection, and correction of the risk polymorphism, e.g., by gene editing of a functional polymorphism that affects expression of NCOA7 may reduce infectivity of a coronavirus. SNP rs11154337 (SEQ ID NO: 1) exists at an intronic region where both the RelA/p65 subunit of NF-kB and STAT1 are predicted to bind. From an antimicrobial defense perspective, this duality suggests a functional cooperation between two host defense pathways: (1) initial detection at the plasma membrane via Toll-like receptors and the NF-kB pathway and (2) potential endosomal pathogen escape that triggers an interferon-mediated response and STAT1/2 activation via Janus tyrosine kinases (JAK). As such, our molecular studies have defined NCOA7 as an upregulated factor in ECs in response to proinflammatory cytokines; moreover, both the inhibition of STAT1/2 signaling via the JAK inhibitor momelotinib and RNAi of RelA/p65 abrogated the IL-1β-mediated upregulation of NCOA7. We have demonstrated that NCOA7 regulates immunoactivation of the endothelium and subsequent leukocyte adhesion and presumable infiltration. To do so, NCOA7 alters lysosomal acidification, a feature that has been independently found to affect entry of other enveloped viruses, such as influenza. Furthermore, utilizing an in vitro biochemical assay of nuclear protein binding to SNP rs11154337 and CRISPR-Cas9-edited, isogenic, inducible-pluripotent stem cell (iPSCs), we have found allele-specific binding to the NF-kB subunit RelA/p65 that drives allele-specific expression of NCOA7.

A lysosome is a membrane-bound organelle found in many animal cells. Lysosomes are spherical vesicles that contain hydrolytic enzymes that can break down many kinds of biomolecules. A lysosome has a specific composition, of both its membrane proteins, and its lumenal proteins. The lumen's pH (~4.5-5.0) is optimal for the enzymes involved in hydrolysis, analogous to the activity of the stomach. Besides degradation of polymers, the lysosome is involved in various cell processes, including secretion, plasma membrane repair, apoptosis, cell signaling, and energy metabolism. Lysosomes act as the waste disposal system of the cell by digesting in used materials in the cytoplasm, from both inside and outside the cell. Material from outside the cell is taken up through endocytosis, while material from the inside of the cell is digested through autophagy. The size of lysosomes varies from 0.1 μm to 1.2 μm. Lysosomes have a pH ranging from ~4.5-5.0, accordingly, the interior of the lysosomes is acidic compared to the slightly basic cytosol (pH 7.2). The lysosome maintains its pH differential by pumping in protons ($H^+$ ions) from the cytosol across the membrane via proton pumps and chloride ion channels. Vacuolar-ATPases are responsible for transport of protons, while the counter transport of chloride ions is performed by ClC-7 $Cl^-/H^+$ antiporter.

The JAK-STAT signaling pathway is a chain of interactions between proteins in a cell, and is involved in processes such as immunity, cell division, cell death and tumour formation. The JAK-STAT pathway communicates information from chemical signals outside of a cell to the cell nucleus, resulting in the activation of genes. There are three key parts of JAK-STAT signaling: Janus kinases (JAKs), signal transducer and activator of transcription proteins (STATs), and receptors (which bind the chemical signals). There are 4 JAK proteins: JAK1, JAK2, JAK3 and TYK2. JAKs contain a FERM domain (approximately 400 residues), an SH2-related domain (approximately 100 residues), a kinase domain (approximately 250 residues) and a pseudokinase domain (approximately 300 residues). The kinase domain is vital for JAK activity, since it allows JAKs to phosphorylate (add phosphate groups to) proteins. There are 7 STAT proteins: STAT1, STAT2, STAT3, STAT4, STAT5A, STAT5B and STAT6. STAT proteins contain many different domains, each with a different function, of which the most conserved region is the SH2 domain. The SH2 domain is formed of 2 α-helices and a β-sheet and is formed approximately from residues 575-680. STATs also have transcriptional activation domains (TAD), which are less conserved and are located at the C-terminus. In addition, STATs also contain: tyrosine activation, amino-terminal, linker, coiled-coil and DNA-binding domains.

The binding of various ligands, usually cytokines, such as interferons and interleukins, to cell-surface receptors, causes the receptors to dimerize, which brings the receptor-associated JAKs into close proximity. The JAKs then phosphorylate each other on tyrosine residues located in regions called activation loops, through a process called transphosphorylation, which increases the activity of their kinase domains. The activated JAKs then phosphorylate tyrosine residues on the receptor, creating binding sites for proteins possessing SH2 domains. STATs then bind to the phosphorylated tyrosines on the receptor using their SH2 domains, and then they are tyrosine-phosphorylated by JAKs, causing the STATs to dissociate from the receptor. These activated STATs form hetero- or homodimers, where the SH2 domain of each STAT binds the phosphorylated tyrosine of the opposite STAT, and the dimer then translocates to the cell nucleus to induce transcription of target genes. STATs may also be tyrosine-phosphorylated directly by receptor tyrosine kinases, but since most receptors lack built-in kinase activity, JAKs are usually required for signaling.

Transcription factor p65, also known as nuclear factor NF-kappa-B p65 subunit, is a protein that in humans is encoded by the RELA gene. RELA, also known as p65, is a REL-associated protein involved in NF-κB heterodimer formation, nuclear translocation and activation. NF-κB is an essential transcription factor complex involved in all types of cellular processes, including cellular metabolism, chemotaxis, etc. Phosphorylation and acetylation of RELA are crucial post-translational modifications required for NF-κB activation. RELA has also been shown to modulate immune responses, and activation of RELA is positively associated with multiple types of cancer.

Momelotinib (formerly GS-0387, CYT-387) is an inhibitor of Janus kinases JAK1 and JAK2, acting as an ATP competitor with IC50 values of 11 and 18 nM, respectively. An exemplary chemical structure of momelotinib is illustrated below:

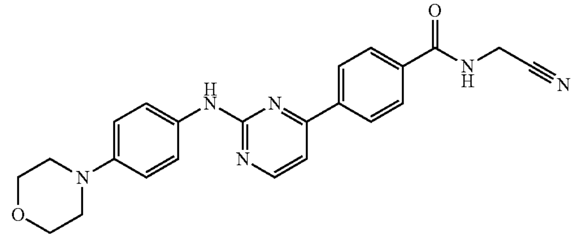 [SMILES: N#CCNC(=O)c1ccc(-c2ccnc(Nc3ccc(N4CCOCC4)cc3)n2)cc1]

Additional inhibitors of JAK signaling include, but are not limited to, tofacitinib, CYT387, baricitinib, ruxolitinib, TG101348, lestaurtinib, AZD1480, R348, VX-509, GLPG0634, GSK2586184, AC-430, pacritinib, or BMS-911543 (Furumoto Y, Gadina M. The arrival of JAK inhibitors: advancing the treatment of immune and hematologic disorders. *BioDrugs*. 2013; 27(5):431-438. doi:10.1007/s40259-013-0040-7).

Provided herein is a method of treating a coronavirus infection in a patient that comprises administering an agent to the patient in an amount effective to increase cellular lysosomal pH in cells of the patient. In some embodiments, the agent is one or more of an agent for reducing expression or activity of a nuclear receptor coactivator 7 (NCOA7) transcript, an RNAi agent or antisense reagent for knocking down expression of a v-rel avian reticuloendotheliosis viral oncogene homolog A (RelA/p65) transcript, a janus kinase (JAK) inhibitor. In some embodiments, the agent increases cellular lysosomal pH in cells of the patient. Other therapeutic agents include small molecule drug compounds and/or binding reagents (e.g. antibody or antibody derivative or fragments, or, aptamers), that cause an increase in lysosomal pH by affecting NCOA7 directly or indirectly via relevant induction pathways, e.g., as described herein.

Further provided herein is a method of reducing infectivity of a coronavirus infection in a cell that comprises administering an agent to the cell in an amount effective to increase cellular lysosomal pH in the cell. In some embodiments, the agent is one or more of an agent for reducing expression or activity of a nuclear receptor coactivator 7 (NCOA7) transcript, an RNAi agent or antisense reagent for knocking down expression of a v-rel avian reticuloendotheliosis viral oncogene homolog A (RelA/p65) transcript, a janus kinase (JAK) inhibitor. In some embodiments, the agent increases cellular lysosomal pH in the cell. Other therapeutic agents include small molecule drug compounds and/or binding reagents (e.g. antibody or antibody derivative or fragments, or, aptamers), that cause an increase in lysosomal pH by affecting NCOA7 directly or indirectly via relevant induction pathways, e.g., as described herein.

For reducing expression, reducing activity, or knocking down expression of a gene, RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as locked nucleic acid or gapped-locked nucleic acid, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered into the cytosol, they are efficiently recognized and stably incorporated into the RNA-induced silencing complex (RiSC) to achieve prolonged gene silencing. Either antisense technology or RNAi may be used effectively to knock-down or silence expression of a gene or gene product, such as HAS2 or HYAL1 (see, e.g., Watts, J. K., et al. Gene silencing by siRNAs and antisense oligonucleotides in the laboratory and the clinic (2012) 226(2):365-379). It should be noted that siRNAs and/or ASOs targeting HAS2 or HYAL1 are commercially available from sources such as Horizon™ or Thermo Fisher Scientific, among many other sources, or are readily determined and synthesized based on broadly-known algorithms and calculators using an appropriate mRNA/cDNA sequence as input, such as, without limitation, SEQ ID NOS: 3-6, 9-12, or the variants thereof. One siRNA, or multiple siRNAs targeting different portions of a target mRNA may be used.

Non-limiting NCOA7 siRNA sequences include sequences with greater than 70, 80, 90, 95, or 98%>sequence identity or similarity to GTGGAAGCAGAGTAGAGAGAA (SEQ ID NO: 3).

Non-limiting NCOA7 siRNA sequences include sequences with greater than 70, 80, 90, 95, or 98%>sequence identity or similarity to GAAGATCATCACTGTTGAAGA (SEQ ID NO: 4).

Non-limiting NCOA7 siRNA sequences include sequences with greater than 70, 80, 90, 95, or 98%>sequence identity or similarity to GGAAUGUCUCAUGAUAUCATT (SEQ ID NO: 9).

Non-limiting NCOA7 siRNA sequences include sequences with greater than 70, 80, 90, 95, or 98%>sequence identity or similarity to UGAUAUCAUGAGACAUUCCTG (SEQ ID NO: 10).

Non-limiting RELA siRNA sequences include sequences with greater than 70, 80, 90, 95, or 98%>sequence identity or similarity to GCTTCTATGAGGCTGAGCTCT (SEQ ID NO: 5).

Non-limiting RELA siRNA sequences include sequences with greater than 70, 80, 90, 95, or 98%>sequence identity or similarity to GCGCATCCAGACCAACAACAA (SEQ ID NO: 6).

Non-limiting RELA siRNA sequences include sequences with greater than 70, 80, 90, 95, or 98%>sequence identity or similarity to CCCUUUACGUCAUCCCUGATT (SEQ ID NO: 11).

Non-limiting RELA siRNA sequences include sequences with greater than 70, 80, 90, 95, or 98%>sequence identity or similarity to UCAGGGAUGACGUAAAGGGAT (SEQ ID NO: 12).

RNAi sequences, for example siRNA sequences, can be readily obtained from commercially sources. By way of example, NCOA7 siRNA sequences can be obtained from ThermoFisher Scientific. Exemplary NCOA7 siRNA sequences can be obtained that target any RNA sequence of human NCOA7. For example and without limitation, ThermoFisher Scientific identifies and sells human NCOA7 siRNA sequence at bases 530, 608, 740, 951, 981, 983, 987, 1089, 2053, 2202, 2225, 2853, 2900, 3433, 3776, 5136, and 5236 of NM_001122842.2 (provided in FIG. 7-1 and FIG. 7-2, SEQ ID NO: 2) that can be used to generate one or more siRNAs targeting human NCOA7. Exemplary RELA siRNA sequences can be obtained that target any RNA sequence of human RELA. Likewise, for example and without limitation, ThermoFisher Scientific identifies and sells human RELA siRNA sequence at bases 297, 716, 793, 805, 985, 1026, 1027, 1029, 1050, 1180, 1187, 1206, 1209, 1621, 1633, 1743 of NM_001145138.1 (provided in FIG. 8, SEQ ID NO: 7) that can be used to generate one or more siRNAs targeting human RELA.

The terms "iRNA," "RNAi agent," "RNAi agent," and "RNA interference agent" as used interchangeably herein, refer to an agent that contains RNA nucleotides, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., knocks down or silences, the expression of NCOA7 or RELA RNA in a cell, e.g., a cell within a subject, such as a mammalian subject.

In one aspect, an RNAi agent includes a single stranded RNAi that interacts with a target RNA sequence, e.g., an NCOA7 or RELA RNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer. Dicer, a ribonuclease-III-like enzyme, processes these dsRNA into 19-23 base pair short interfering RNAs with characteristic two base 3' overhangs. These siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. Thus, in one aspect an RNAi is a single stranded RNA (ssRNA) (the antisense strand of an siRNA duplex) generated within a cell and which promotes the formation of a RISC complex to effect silencing of the target gene. Accordingly, the term "siRNA" is also used herein to refer to an interfering RNA (iRNA).

In another aspect, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) *Cell* 150:883-894.

In another aspect, an "iRNA" or RNAi agent" for use in the compositions and methods described herein is a double stranded RNA and can be referred to herein as a "double stranded RNAi agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, e.g., an NCOA7 or RELA RNA. In some aspects, a double stranded RNA (dsRNA) triggers the degradation of a target RNA, e.g., an mRNA, through a post-transcriptional gene-silencing mechanism referred to herein as RNA interference or RNAi.

The majority of nucleotides of each strand of a dsRNA molecule may be ribonucleotides, but as described in detail herein, each or both strands can also include nucleotide analogs, where one or more non-ribonucleotides, e.g., a deoxyribonucleotide and/or a modified nucleotide. In addition, as used in this specification, an "RNAi agent" or "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified inter-nucleotide linkage, and/or modified nucleobase. Thus, the term modified nucleotide encompasses substitutions, additions or removal of, e.g., a functional group or atom, to inter-nucleoside linkages, sugar moieties, or nucleobases. The modifications suitable for use in the agents described herein include all types of modifications disclosed herein or known in the art. Any such modifications, as used in a siRNA type molecule, are encompassed by "RNAi agent" or "RNAi reagent" for the purposes of this disclosure.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some aspects, the hairpin loop can comprise at least 2, at least 3, at least 4, at least 5, at least 6, at least 7, at least 8, at least 9, at least 10, at least 20, at least 23, or more unpaired nucleotides. In some aspects, the hairpin loop can be 10 or fewer nucleotides. In some aspects, the hairpin loop can be 8 or fewer unpaired nucleotides. In some aspects, the hairpin loop can be 4-10 unpaired nucleotides. In some aspects, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one aspect, an RNAi agent is a dsRNA, each strand of which comprises 19-23 nucleotides, that interacts with a target RNA sequence, e.g., an NCOA7 or RELA RNA, without wishing to be bound by theory, long double stranded RNA introduced into cells is broken down into siRNA by a Type III endonuclease known as Dicer. Dicer, a ribonuclease-III-like enzyme, processes the dsRNA into 19-23 base pair short interfering RNAs with characteristic two base 3' overhangs. The siRNAs are then incorporated into an RNA-induced silencing complex (RISC) where one or more helicases unwind the siRNA duplex, enabling the complementary antisense strand to guide target recognition. Upon binding to the appropriate target RNA, one or more endonucleases within the RISC cleave the target to induce silencing. In one aspect, an RNAi agent is a dsRNA of 24-30 nucleotides that interacts with a target RNA sequence, e.g., an HAS2 or HYAL1 RNA sequence, to direct the cleavage of the target RNA.

In addition to siRNA, small hairpin RNAs (shRNA) may be delivered to a patient for treatment as described herein. shRNA are sequences of RNA, typically about 80 base pairs in length, that include a region of internal hybridization that creates a hairpin structure. shRNA molecules are processed within the cell to form siRNA, which in turn knock down gene expression. shRNA is that they can be incorporated into viral vectors for short-term, or long-term expression in a cell. As with shRNA, antisense sequences may be expressed by the gene of a recombinant virus particle.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary," and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of a messenger RNA (mRNA)" refers to a polynucleotide that is substantially complementary to a contiguous portion of the mRNA of interest (e.g., an NCOA7 or RELA RNA).

Accordingly, in some aspects, the antisense strand polynucleotides disclosed herein are fully complementary to the target NCOA7 or RELA RNA sequence. In other aspects, the antisense strand polynucleotides disclosed herein are substantially complementary to the target NCOA7 or RELA RNA sequence and comprise a contiguous nucleotide sequence which has at least about 80% sequence identity to the nucleotide sequence of any of SEQ ID NOS: 3-6, 9-12, or a fragment thereof, such as about 85%, about 86%, about 87%, about 88%, about 89%, about 90%, about 91%, about 92%, about 93%, about 94%, about 95%, about 96%, about 97%, about 98%, or about 99% complementary.

It is understood that the sequence of the NCOA7 or RELA RNA must be sufficiently complementary to the antisense strand of the RNAi agent for the agent to be used in the indicated patient, e.g. human, mammalian, or vertebrate species.

The term "inhibiting," as used herein, is used interchangeably with "reducing," "silencing," "downregulating," "suppressing," "knocking down," and other similar terms, and includes any level of inhibition.

The phrase "reducing expression, reducing activity, or knocking down (or silencing) of NCOA7 or RELA RNA," as used herein, includes inhibition of expression of any NCOA7 or RELA gene (such as, e.g., a mouse NCOA7 or RELA gene, a rat NCOA7 or RELA gene, a monkey NCOA7 or RELA gene, or a human NCOA7 or RELA gene) as well as variants or mutants of an NCOA7 or RELA gene, in its production of NCOA7 or RELA RNA, affecting the stability of NCOA7 or RELA RNA, such as by antisense or RNAi technologies. "Knocking down (or silencing) of NCOA7 or RELA RNA" includes any level of inhibition of an NCOA7 or RELA RNA, e.g., at least partial suppression of the expression of an NCOA7 or RELA RNA, such as an inhibition by at least about 20%. In certain aspects, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an NCOA7 or RELA RNA may be assessed based on the level of any variable associated with NCOA7 or RELA RNA expression, e.g., NCOA7 or RELA RNA level. The expression of an NCOA7 or RELA RNA may also be assessed indirectly based on assay of physiological markers associated with decreased expression of the NCOA7 or RELA RNA in a patient.

In one aspect, at least partial suppression of the expression of an NCOA7 or RELA RNA, is assessed by a reduction of the amount of NCOA7 or RELA RNA that can be isolated from or detected in a cell or group of cells, e.g., in a cardiovascular cells. A reduction of the amount of NCOA7 or RELA RNA in a cell or tissue in which an NCOA7 or RELA gene is transcribed and which has been treated such that the expression of an NCOA7 or RELA RNA is inhibited, may be determined as compared to a second cell or tissue substantially identical to the first cell or tissue but which has not been so treated (control cells), e.g., obtained and cultured from a biopsy. The degree of inhibition may be expressed in terms of:

$$\left( \frac{(mRNA \text{ in control cells}) - (mRNA \text{ in treated cells})}{(mRNA \text{ in control cells})} \times 100\% \right)$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell. Further, an shRNA RNAi agent can be produced from a gene for expressing an shRNA, transferred by any suitable means, such as by recombinant vector such as a recombinant adenovirus, Adeno-associated virus (AAV), or retrovirus vector, or by gene editing, such as by CRISPR-Cas or TALENS methods, as are broadly-known. These technologies are broadly-known by those of ordinary skill and resources, such as suitable vectors and production systems are broadly-available, including from commercial sources.

While other viral vectors and methods of their production and use are broadly-known, the following discusses, as a non-limiting example, adenoviral vectors. An adenoviral vector may be replication-competent, conditionally replication-competent or replication-deficient in host cells or in therapeutic target cells. The adenoviral vector can comprise a gene for expression of an shRNA sequence. Methods of making, propagating, and using adenovirus vectors and adenovirus particles are broadly-known, with many suitable vectors being described in publications and being available commercially. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) may be used to generate the adenoviral vector. For example, a simian adenovirus can be used as the source of the viral genome of the adenoviral vector. A simian adenovirus may be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. A chimpanzee serotype C Ad3 vector may be used (see, e.g., Peruzzi D, et al. A novel chimpanzee serotype-based adenoviral vector as delivery tool for cancer vaccines. Vaccine. 2009; 27(9):1293-1300) or an Ad5 vector may be used. Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Non-limiting examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/022311.

Contacting a cell in vitro may be done, for example, by incubating the cell with the RNAi agent. Contacting a cell in vivo may be done, for example, by injecting or placing the RNAi agent into or near the tissue where the cell is located, such as a tumor, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, which directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one aspect, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by use of auxiliary agents or devices. Introducing an iRNA into a cell may be in vitro and/or in vivo. For example, for in vivo introduction, iRNA can be injected into a tissue site or administered systemically. In vitro introduction into a cell includes methods known in the art such as electroporation and lipofection. Further approaches are known in the art.

As used herein, and further to the discussion above regarding iRNA reagents, "agent" or "RNAi agent," when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) J Clin Invest. 117(12):3615-3622, also describing RNAi, and United States Patent Application Publication No. 2017/0081667, incorporated herein by reference for its technical disclosure). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to those NCOA7- or RELA-active RNAi agents described herein, antisense agents (ASOs), other RNAi agents, ribozyme agents, and other nucleic acid-based methods of reducing gene expression, can be designed and tested based on known sequences of NCOA7- or RELA RNAs and gene structure (exemplary sequences are provided herein). Based on the present disclosure, one of ordinary skill can design, and/or produce an active agent capable of knocking down NCOA7 or RELA expression. Of note, a number of publications describe algorithms for generating candidate iRNA sequences, and publicly-available software can be used to implement those algorithms. As such, typically, one only needs to enter an mRNA sequence into a calculator to produce candidate iRNAs.

As above, RNAi reagents, such as an siRNA, may have 100% sequence identity with a portion or fragment of any one or more of SEQ ID NOS: 3-6, 9-12, or a sequence complementary thereto, or may include one or more additional nucleobases at their 3' or 5' end, or may include one or more substitutions that do not substantially interfere with the activity of the RNAi agent in knocking down or silencing NCOA7 or RELA expression. Also, SEQ ID NOS: 3-6 and 9-12 are exemplary mRNAs of NCOA7 or RELA. Alleles, mutations, or other variants or polymorphisms (e.g., single-nucleotide polymorphisms, SNPs) of NCOA7- or RELA sequences are possible, and as such effective agents, such as RNAi and antisense agents may be substituted to accommodate those variants. Further, some sequence mismatches in RNAi agents are not only tolerated, but may be beneficial (see, e.g., Wu, H., et al. "Improved siRNA/shRNA Functionality by Mismatched Duplex" *PLoS One*. 2011; 6(12): e28580). As such, sequences having up to 90% or 95% (two or one mismatches, respectively) sequence identity with SEQ ID NOS: 3-6 and 9-12 are expected, in many circumstances, to be effective RNAi agents.

In aspects, a useful antisense oligonucleotide, e.g., a nucleic acid or nucleic acid analog, comprises a sequence having at least 90% sequence identity, at least 95% sequence identity, or 100% sequence identity with one of SEQ ID NOS: 3-6 and 9-12. In aspects, the antisense oligonucleotide is an LNA.

As described above, design and implementation of interfering RNA and antisense reagents useful in knocking down expression of a target gene, such as NCOA7- or RELA are well within the skill of an ordinary artisan, with commercial sources and design methods being broadly-available. siRNA targeting specific mRNAs are broadly-available commercially, and methods of determining and testing potential siRNA candidates are broadly-available, commercial, and otherwise (see, e.g., Tuschl T. Expanding small RNA interference. *Nature Biotech* 2002; 20:446-8 and Hu B, et al.

Therapeutic siRNA: state of the art. *Signal Transduct Target Ther.* 2020 Jun. 19; 5(1):101). These references provide a roadmap as to how to design, make, and use RNAi (RNA interference) reagents, including nucleic acid modifications, shRNA delivery systems and vectors, and pharmaceutical formulations, such as lipid nanoparticles.

In examples, siRNA, as well as other nucleic acid-based therapeutics such as naked DNA and ASO reagents, may be delivered using lipid nanoparticles, which are efficient carriers of cargo, such as a nucleic acid cargo, for delivery into cells for gene delivery, mRNA delivery, antisense, RNA interference, among other uses. Lipid nanoparticles typically comprise helper lipids, cholesterol, ionizable lipids (e.g., lipidoids), lipid-polymer conjugates and nucleic acid cargo. Lipid nanoparticles may be administered in an intravenous, intramuscular or subcutaneous injection. Exemplary LNP compositions and/or compositions, e.g., lipidoids, useful in producing LNPs are described in U.S. Pat. Nos. 10,844,028, 10,189,802, 9,872,911, 9,556,110, 9,439,968, 9,227,917, 8,969,353, and 8,450,298, as well as in U.S. Patent Application Publication Nos. 20170204075, 20190177289, 20170152213, 20160114042, 20150203439, 20140322309, 20140161830, 20110293703, and 20100331234, each of which incorporated herein by reference for its technical disclosure relating to compounds and compositions useful in delivery of nucleic acid cargoes, and to the extent it is consistent with the present disclosure. Additional examples of lipid nanoparticles are described in U.S. Pat. Nos. 9,404, 127, 9,364,435, and 8,058,069, each of which incorporated herein by reference for its technical disclosure relating to compounds and compositions useful in delivery of nucleic acid cargoes, and to the extent it is consistent with the present disclosure (see, also, e.g., Sabnis S, et al., A Novel Amino Lipid Series for mRNA Delivery: Improved Endosomal Escape and Sustained Pharmacology and Safety in Non-human Primates. *Mol Ther.* 2018; 26(6):1509-1519 and Yonezawa S, et al. Recent advances in siRNA delivery mediated by lipid-based nanoparticles. *Adv Drug Deliv Rev.* 2020; 154-155:64-78). The BNT162b2 and mRNA-1273 COVID9 vaccines are formulated as lipid nanoparticles. Examples of lipid nanoparticles, lipidoids, and methods of making lipid nanoparticles and lipidoids, as described herein, are described in Whitehead K A, et al. Degradable lipid nanoparticles with predictable in vivo siRNA delivery activity. *Nat Commun.* 2014 Jun. 27; 5:4277.

FIG. 7-1 and FIG. 7-2 provides an exemplary mRNA sequence for human NCOA7 (GenBank Accession No. NM_001199622.2, e.g., NCOA7 [*Homo sapiens* (human)]).

As with RNAi therapeutics antisense technology is mature and one of ordinary skill can develop suitable reagents for production of antisense oligonucleotides able to target specific genes, such as NCOA7 or RELA. (Quemener A M, et al. The powerful world of antisense oligonucleotides: From bench to bedside. Wiley Interdiscip Rev RNA. 2020 September; 11(5):e1594; Antisense LNA® GapmeRs Handbook, Qiagen, October 2017; and Shen X, et al., Chemistry, mechanism and clinical status of antisense oligonucleotides and duplex RNAs. Nucleic Acids Res. 2018; 46(4):1584-1600). Commercial sources of gene-specific development services for antisense reagents include, without limitation Ionis Pharmaceuticals, Inc., among others.

Further provided herein is a method of reducing, treating, or preventing a coronavirus infection in a patient that comprises administering an agent to the patient in an amount effective to reduce, knock down, or knock out expression of a nuclear receptor coactivator 7 (NCOA7) transcript thereby increasing cellular lysosomal pH of the patient, further comprising quantifying the NCOA7 transcript by at least one of sequencing, PCR, probe-binding, or factor-binding of the NCOA7 transcript. In some embodiments, the methods provided herein further comprises obtaining genetic data (by one or more of sequencing, PCR, probe-binding, or factor-binding) for the patient and determining if the patient has one or two alleles for C at rs11154337.

As will be understood by one of skill in the art, sequencing, or DNA sequencing, is the process of determining the nucleic acid sequence—the order of nucleotides in DNA. Sequencing includes any method or technology (for example, polymerase chain reaction (PCR) sequencing, probe-binding sequencing, or factor-biding sequencing) that is used to determine the order of the four bases: adenine, guanine, cytosine, and thymine.

In another aspect or embodiment, a method of treating a patient having increased susceptibility to a coronavirus infection is provided. The method comprises measuring a nuclear receptor coactivator 7 (NCOA7) transcript having SEQ ID NO: 1, or a complementary sequence thereof, by at least one of sequencing, PCR, probe-binding, or factor-binding of the NCOA7 transcript.

According to another aspect or embodiment of the invention, a method of reducing infectivity of a coronavirus infection in a cell is provided. The method comprising administering an agent to the cell in an amount effective to reduce expression of a nuclear receptor coactivator 7 (NCOA7) transcript thereby increasing lysosomal pH in the cells.

Example 1

SARS-CoV-2 is a highly contagious, novel coronavirus that is complicated by severe respiratory manifestations and death in a percentage of infected individuals. Among those infected, there is a higher prevalence and severity of SARS-CoV-2 disease in persons with co-morbid cardiovascular disease, such as hypertension and diabetes. Furthermore, >7% of patients suffer myocardial and cardiovascular injury from infection (22% of the critically ill), particularly as disease severity intensifies. Recently, it has been reported that the SARS-CoV-2 spike protein can bind and utilize the angiotensin-converting enzyme 2 (ACE2) receptor for entry into human cells. In addition to pulmonary epithelial, brain, mucosal, and renal cells, cardiomyocytes and vascular endothelial cells express ACE2. However, data regarding direct SARS-CoV-2 infection of any cardiovascular cell type are lacking, and it is unclear whether factors that control viral entry into cardiovascular cells underlie SARS-CoV-2 disease characteristics. Thus, pressing questions abound regarding the molecular controls of viral entry that move beyond the direct binding of SARS-CoV-2 to ACE2.

Do factors that control lysosomal acidification alter SARS-CoV-2 entry into cardiovascular cells? Similar to other coronaviruses, it is thought that upon binding ACE2, SARS-CoV-2 enters via an endosomal encapsulation pathway dependent upon lysosomal acidification. Interestingly, the putative effects of hydroxychloroquine in preventing infection may also rely upon altered lysosomal pH. However, the crucial molecules that regulate lysosomal pH and viral entry into cardiovascular cells have not been defined. Identification of such molecules may serve as a crucial foundation for the development of therapeutic drugs to combat this pandemic.

Do genetic variants in lysosomal acidification factors confer protection or susceptibility to SARS-CoV-2 entry? It is possible that functional genetic variants (e.g., SNPs) in molecules that regulate lysosomal acidification in cardiovascular cells may confer cellular protection or susceptibility to viral entry, thereby accounting for the wide and unexplained variation of disease severity in the global population.

Over the last two years, our lab has been investigating the endothelial cell (EC) pathobiology of the nuclear receptor coactivator 7 (NCOA7), a gene carrying a candidate SNP (rs11154337) located in the promoter of an interferon-inducible isoform of this factor (NCOA7short), and one that we identified in an unpublished genome-wide association study (GWAS) of survival in human pulmonary arterial hypertension. Interestingly, SNP rs11154337 exists at an intronic region where both the RelA/p65 subunit of NF-κB and STAT1 are predicted to bind. From an antimicrobial defense perspective, this duality suggests a functional cooperation between two host defense pathways: (1) initial detection at the plasma membrane via Toll-like receptors and activation of the NF-κB pathway and (2) potential endosomal pathogen escape that triggers an interferon-mediated response and STAT1/2 activation via Janus tyrosine kinases (JAK). In line with this notion, our molecular studies have defined NCOA7 as an upregulated factor in ECs in response to proinflammatory cytokines (FIGS. 1A-1B (SEQ ID Nos: 9-10) and FIGS. 2A-2C); moreover, both the inhibition of STAT1/2 signaling via the JAK1/2 inhibitor momelotinib (in Phase III clinical trials) and RNAi of RelA/p65 (SEQ ID Nos: 11-12) abrogated the IL-1β-mediated upregulation of NCOA7 (FIGS. 3A-3C and FIGS. 4A-4C). We have demonstrated that NCOA7 regulates immunoactivation of the endothelium and subsequent leukocyte adhesion and presumable infiltration (FIGS. 1A-1B and FIGS. 2A-2C). To do so, NCOA7 alters lysosomal acidification, a feature that has been independently found to affect entry of certain other enveloped viruses, such as influenza. Furthermore, utilizing an in vitro biochemical assay of nuclear protein binding to SNP rs11154337 and CRISPR-Cas9-edited, isogenic, inducible-pluripotent stem cell (iPSCs), we have found allele-specific binding to the NF-κB subunit RelA/p65 that drives allele-specific expression of NCOA7 (FIGS. 3A-3C and FIGS. 4A-4C).

Example 2

Define the causative role of NCOA7 for SARS-CoV-2 viral entry to primary ECs. Based on our preliminary data (FIGS. 1A-1B, FIGS. 2A-2C, FIGS. 3A-3C, and FIGS. 4A-4C), we will determine whether NCOA7 and its control of lysosomal acidification alters SARS-CoV-2 viral entry to ECs and cardiomyocytes. To do so, we will utilize a platform of creating pseudotyped viruses, as described, carrying the SARS-CoV-2 spike protein on its envelope surface but with a lentiviral backbone carrying either GFP or a puromycin resistance gene. Our lab carries cloned expression vectors for the spike protein from both the Wuhan (Sino Biological) and German epidemics, which are similar in protein sequence (~76%) but not entirely identical. Viral entry by such replication-incompetent GFP viruses, as dictated by the SARS-CoV-2 spike protein, can be quantified via flow cytometry or fluorescence microscopy; alternatively, cellular survival in puromycin can be scored for Puro$^+$ cells. These viruses are standardly produced by our lab for gene transfer experiments in ECs and cardiomyocyte and do not require more than BSL2$^+$ safety standards.

As in our preliminary data, using primary human vascular ECs as well as iPSC-derived cardiomyocytes, we will utilize gain-of-function (e.g., lentiviral delivery) and loss-of-function methodologies (e.g., RNAi of NCOA7 or momelotinib treatment) to force NCOA7 expression and knockdown during IL-1β exposure when NCOA7 is upregulated. In these contexts, we will expose cells to pseudotyped SARS-CoV-2 virus, followed by quantification of viral infection, along with assessment of lysosomal acidification (FIGS. 1A-1B and FIGS. 2A-2C).

We expect that increased NCOA7 will enhance lysosomal acidification (e.g., decrease pH) and promote SARS-CoV-2 entry. Conversely, RNAi against upregulated NCOA7 (SEQ ID Nos: 9-10) or momelotinib treatment will lead to reduced lysosomal acidification (e.g., increased pH) and abrogate SARS-CoV-2 entry. If so, we are prepared to test the ability for NCOA7 to control live replication-competent SARS-CoV-2 cellular infection. Furthermore, we are prepared to modulate ACE2 expression to better understand the relationship between expression of NCOA7 and ACE2-mediated, SARS-CoV-2 entry. We expect that NCOA7 will carry actions across cardiovascular cell types; however, it is possible that some cell types may be more permissive to the actions of NCOA7, offering insight into tissue-specific effects of viral entry. It is also possible that the Wuhan vs. German SARS-CoV-2 viral spike protein may display differences in viral entry and dependence on NCOA7 and ACE2. These data may explain the differences observed in severity and transmissibility across the regional contexts of this pandemic. Finally, if successful, our team already carries the NCOA7-/- mouse for future study of live replication-competent SARS-CoV-2 infection and putative NCOA7-specific alteration of in vivo cardiopulmonary complications.

Example 3

Via specific CRISPR-Cas9-edited iPSC-ECs, determine the causative role of NCOA7 SNP rs11154337 in controlling NCOA7 expression and SARS-CoV-2 viral entry. Based on our preliminary data (FIGS. 1A-1B, FIGS. 2A-2C, FIGS. 3A-3C, and FIGS. 4A-4C), we postulate that, by decreasing expression of NCOA7, the G allele of SNP rs11154337 increases lysosomal pH and abrogates SARS-CoV-2 entry. To investigate, we plan to differentiate the isogenic iPSC lines (FIG. 4B) carrying either alleles into either ECs (as in FIGS. 3A-3C, and FIGS. 4A-4C) or cardiomyocytes. These cells will then be exposed to pseudotyped SARS-CoV-2 as described above for assessment of lysosomal acidification and viral entry.

In both iPSC-derived ECs and cardiomyocytes, we anticipate that the G allele of SNP rs11154337 will reduce NCOA7 expression, decrease lysosomal acidification rate, and abrogate SARS-CoV-2 entry. If so, these data would comprise crucial evidence of a causative and allele-specific action of this SNP that confers cellular susceptibility to viral entry and could explain the unexplained variation of disease severity in the global population.

Example 4

Via targeted SNP sequencing of PBMCs from SARS-CoV-2$^+$ patients with severe vs. mild/asymptomatic cardiovascular manifestations, investigate for an association of SNP rs11154337 in disease severity. Based on our preliminary data (FIGS. 1A-1B, FIGS. 2A-2C, FIGS. 3A-3C, and FIGS. 4A-4C) suggesting that NCOA7 can modulate viral entry with implications on disease manifestation, we postulate an association of SNP rs11154337 with SARS-CoV-2 disease severity. To investigate, we plan to genotype this SNP in SARS-CoV-2±infected persons in the UPMC hospital system. We plan a SNP association study comparing persons with severe cardiovascular manifestations vs. without symptoms. Inclusion criteria for severe cardiovascular manifestations include SARS-CoV-2+ 18 to 50-year-old patients without prior co-morbidities in intensive care with newly decreased left ventricular ejection fraction <30% by echocardiography or sudden cardiac death. SARS-CoV-2+, asymptomatic patients will include 18 to 50-year-old persons without prior co-morbidities, subjective symptoms, and hospitalization. Access is available to genomic samples of >9,000 sequenced patients where the electronic health record can be used to identify asymptomatic/mild and severe cases.

In this pilot study, we postulate that the G allele of SNP rs11154337 will associate with decreased risk of severe cardiovascular disease after SARS-CoV-2 infection. Pennsylvania Department of Health data (as of Mar. 27, 2020) shows that 26% of adults with COVID-19 needs hospital admission. A sample size of 50 severe vs. 100 non-severe has 80% power ($\alpha$=0.05, two-sided test) to significantly estimate an odds ratio of 2.4 (with a GG frequency of 25% in non-severe group). A centralized repository of blood samples is planned throughout the over the next year. If recruitment numbers become challenging, we can plan to relax restrictions on co-morbidities of participants; but for now, such criteria will aid in controlling for confounders. It is also possible that this SNP may affect transmissibility more than disease severity. If so, we are prepared to recruit separate cohorts to study populations that were infected after single exposures vs. those that resisted infection despite multiple exposures. Finally, to ensure recruitment, we also have the ability to attain additional samples.

Example 5

Develop novel inhibitors and repurpose existing JAK1 inhibitors that decrease NCOA7 to abrogate SARS-CoV-2 infection. This work would serve as the foundation for initiating the development/repurposing of small molecules or RNAi-based systems that are desperately needed for prevention and/or treatment of SARS-CoV-2-specific cardiopulmonary disease. These include the JAK1/2 inhibitor momelotinib already used in previous Phase III clinical trials.

Utilize NCOA7 SNP genotyping to identify persons at high- and low-risk of SARS-CoV-2 infection and disease severity and offering the foundation for genome editing for disease prevention in humans. If successful, this work could stimulate a rapid global response to SNP genotype individuals. Such information would be transformational to public health initiatives to prioritize protective measures for those at-risk individuals for severe cardiopulmonary compromise. It could also introduce the opportunity for CRISPR/CaS9 genome editing to prevent infection and complications in humans.

Notably, our data offer the ability to pursue a compelling mechanistic hypothesis to explain the puzzling global variation of disease severity in this pandemic—a point that should differentiate this application from large scale but otherwise non-specific observational studies of SARS-CoV-2 infected cells or individuals. Our advanced technology and expertise in the proposed methodology also ensure feasibility of this project, despite the challenges introduced by this pandemic that would traditionally compromise more typical research endeavors.

There have been no prior initiatives exploring the relationship of NCOA7 and its functional SNP rs11154337 to SARS-CoV-2 viral entry in cardiovascular cells. If successful, results would shift the paradigm in describing how the virus infects cells and how certain human genetic variants regulates these viral actions. Finally, the outcomes of this study would be immediately relevant for public health initiatives to identify at-risk individuals and to develop new therapeutics targeting NCOA7.

Example 6

Our data demonstrate in iPSC-derived ECs the presence of a G allele (C/G) versus the wildtype control (C/C) results in decreased expression of NCOA7. Therefore, individuals with lowered NCOA7 expression secondary to the presence of a G allele should confer some protection from infection/disease severity, and individuals with the C alleles (e.g., allowing for higher NCOA7 expression) should have higher rates of infectivity or disease severity: Highest Risk: C/C→C/G→G/G: Lowest Risk. Note that C is the reference allele; C=0.4817 and G is the alternate allele; G=0.5183.

FIG. 6 depicts the location of rs11154337, C allele (top strand) shown. The sequence provided can be used to produce reagents useful in gene editing. Additional flanking sequences include:

(SEQ ID NO: 1)
TGGTAAAAGCCAGGTTGAAGTGGAAAGGAAGGGCATGTGTCTAGTTTATG

CCTCTTTATCCAGCTTGATCTGTGTCTTCAAATATATAGCAGGATAGGGA

[C/G]

TCCATAGTCATGTCCCTGAATGGGAAGACACCTCCTGGCCAGTATCCTTG

CCAAGGTAAACACTGTCAAATGATCATTTTCTTGGTTTAGAATAGCAAA

T.

Other mutations or polymorphisms located in the same intron as rs11154337, e.g., as shown in FIG. 6, or in linkage disequilibrium (e.g., $D_{AB}\neq0$ (non-random association) or $D_{AB}>0$ (positive association), where $D_{AB}=0$ denotes statistical independence) with rs11154337 may either be indicative of a high risk genotype and may functionally affect expression of NCOA7, and therefore may be, like rs11154337 or in combination therewith, useful in detecting persons especially susceptible to coronavirus infection, and correction of the risk polymorphism, e.g., by gene editing of a functional polymorphism that affects expression of NCOA7 may reduce infectivity of a coronavirus.

Having described this invention, it will be understood to those of ordinary skill in the art that the same can be performed within a wide and equivalent range of conditions, formulations and other parameters without affecting the scope of the invention or any embodiment thereof.

The invention claimed is:

1. A method of treating a coronavirus infection in a patient, comprising, administering an agent to the patient in an amount effective to increase cellular lysosomal pH in cells of the patient, wherein the agent is one or more of:
 an RNAi agent or antisense reagent for knocking down expression of an NCOA7 transcript in the patient;
 an RNAi agent or antisense reagent for knocking down expression of a v-rel avian reticuloendotheliosis viral oncogene homolog A (RelA/p65) transcript; or
 a janus kinase (JAK) inhibitor,
 thereby increasing cellular lysosomal pH in cells of the patient,
 wherein the JAK inhibitor is one or more of momelotinib, tofacitinib, CYT387, baricitinib, ruxolitinib, TG101348, lestaurtinib, AZD1480, R348, VX-509, GLPG0634, GSK2586184, AC-430, pacritinib, and BMS-911543.

2. The method of claim 1, wherein the agent effective to increase cellular lysosomal pH in cells of the patient is an RNAi agent or antisense reagent for knocking down expression of an NCOA7 transcript.

3. The method of claim 1, wherein the agent effective to increase cellular lysosomal pH in cells of the patient is an RNAi agent specific to the NCOA7 transcript comprising one or more of an siRNA, an shRNA, or a combination thereof.

4. The method of claim 1, wherein the agent effective to increase cellular lysosomal pH in cells of the patient is an antisense oligonucleotide (ASO).

5. The method of claim 1, wherein the agent effective to increase cellular lysosomal pH in cells of the patient is an RNAi agent or antisense reagent for knocking down expression of a v-rel avian reticuloendotheliosis viral oncogene homolog A (RelA/p65) transcript.

6. The method of claim 5, wherein the RNAi agent or antisense agent is an siRNA, an shRNA, or a combination thereof, specific to a v-rel avian reticuloendotheliosis viral oncogene homolog A (RelA/p65) transcript.

7. The method of claim 1, wherein the agent effective to increase cellular lysosomal pH in cells of the patient is a janus kinase (JAK) inhibitor, wherein the JAK inhibitor is one or more of momelotinib, tofacitinib, CYT387, baricitinib, ruxolitinib, TG101348, lestaurtinib, AZD1480, R348, VX-509, GLPG0634, GSK2586184, AC-430, pacritinib, and BMS-911543.

8. The method of claim 7, wherein the JAK inhibitor is momelotinib.

9. The method of claim 1, further comprising obtaining genetic data for the patient and determining if the patient has one or two alleles for C at rs11154337.

10. The method of claim 1, further comprising determining if the patient has one or two alleles for C at rs11154337.

11. The method of claim 1, wherein the patient has one or two alleles for C at rs11154337.

12. The method of claim 1, wherein treating the coronavirus infection comprises reducing the severity of one or more symptoms of the coronavirus infection.

13. The method of claim 1, wherein the coronavirus infection is one or more of Middle East Respiratory Syndrome Coronavirus (MERS-CoV), Severe Acute Respiratory Syndrome Coronavirus-2 (SARS-CoV-2), or a disease caused thereby.

14. The method of claim 13, wherein the coronavirus is SARS-CoV-2.

15. A method of reducing infectivity of a coronavirus infection in a cell, comprising, administering an agent to the cell in an amount effective to increase cellular lysosomal pH in the cell, wherein the agent is one or more of:
 an RNAi agent or antisense reagent for knocking down expression of an NCOA7 transcript in the cell of a patient;
 an RNAi agent or antisense reagent for knocking down expression of a v-rel avian reticuloendotheliosis viral oncogene homolog A (RelA/p65) transcript; or
 a janus kinase (JAK) inhibitor,
 thereby increasing cellular lysosomal pH in the cell,
 wherein the JAK inhibitor is one or more of momelotinib, tofacitinib, CYT387, baricitinib, ruxolitinib, TG101348, lestaurtinib, AZD1480, R348, VX-509, GLPG0634, GSK2586184, AC-430, pacritinib, and BMS-911543.

16. The method of claim 15, wherein the agent effective to increase cellular lysosomal pH in cells of the patient is an agent for reducing expression or activity of NCOA7 in the patient, wherein the agent effective to increase cellular lysosomal pH in cells of the patient is an RNAi agent or antisense reagent for knocking down expression of an NCOA7 transcript.

17. The method of claim 15, wherein the agent effective to increase cellular lysosomal pH in cells of the patient is an RNAi agent or antisense reagent for knocking down expression of a v-rel avian reticuloendotheliosis viral oncogene homolog A (RelA/p65) transcript.

18. The method of claim 15, wherein the agent effective to increase cellular lysosomal pH in cells of the patient is a janus kinase (JAK) inhibitor.

19. The method of claim 15, wherein the coronavirus infection is one or more of Middle East Respiratory Syndrome Coronavirus (MERS-CoV), Severe Acute Respiratory Syndrome Coronavirus-2 (SARS-CoV-2), or a disease caused thereby.

\* \* \* \* \*